United States Patent [19]

Sandrock et al.

[11] Patent Number: 5,428,061

[45] Date of Patent: * Jun. 27, 1995

[54] ORGANIC NITRATES AND METHOD FOR THEIR PREPARATION

[75] Inventors: Klaus Sandrock, Langenfeld; Joachim Hütter, Leverkusen; Eike Noack, Neuss, all of Germany

[73] Assignee: Schwarz Pharma AG, Monheim, Germany

[*] Notice: The portion of the term of this patent subsequent to Feb. 8, 2011 has been disclaimed.

[21] Appl. No.: 116,946

[22] Filed: Sep. 7, 1993

Related U.S. Application Data

[63] Continuation of Ser. No. 818,502, Jan. 8, 1992, abandoned, which is a continuation-in-part of Ser. No. 406,165, Sep. 12, 1989, abandoned.

[30] Foreign Application Priority Data

Sep. 15, 1988 [DE] Germany ............... 38 31 311.1

[51] Int. Cl.⁶ ................................................ A61K 31/21
[52] U.S. Cl. ...................................... 514/509; 514/432; 514/445; 549/28; 549/64; 558/482; 558/483
[58] Field of Search ................. 558/483, 482; 514/509, 514/432, 445; 549/28, 64

[56] References Cited

U.S. PATENT DOCUMENTS

| | | | |
|---|---|---|---|
| 4,863,949 | 9/1989 | Simon et al. | 514/418 |
| 4,900,719 | 2/1990 | Meano | 514/18 |
| 4,914,129 | 5/1990 | Buhlmayer | 514/616 |
| 5,037,849 | 8/1991 | Simon et al. | 514/509 |

FOREIGN PATENT DOCUMENTS 0052910 11/1981 European Pat. Off. .
1078045 2/1966 United Kingdom .

OTHER PUBLICATIONS

Gould Medical Dictionary, p. 363, 1972.
Campbell et al "Preparation and reaction of nitrate esters . . . " Chem Abst. 78(21):136650e (1973) & structure of RN 38660-08-01.
JP02091054 Chem Abstract 113(23):212672x Mar. 1990.
Stryer, *Biochemistry*, p. 343, 1981.
Burger, *Medicinal Chemistry*, p. 75, 1970.
J.P. 58,62,147 Chem Abs. 100 34135 (1984).
Campbell et al, J. Org. Chem., vol. 38, No. 6, 1973, pp. 1183–1186.
M. Portelli, G. Renzi, G. Vervato—IL FARMACO Edizione Scientifica Anno XXXI N. 11, Nov. 1976, Ed. Sc. vol. 31 "Synthesis of N–acetylcysteine Compounds" pp. 767–775.

*Primary Examiner*—Peter O'Sullivan
*Assistant Examiner*—Brian M. Burn
*Attorney, Agent, or Firm*—Marshall, O'Toole, Gerstein, Murray & Borun

[57] ABSTRACT

New organic nitrate compounds, formed by condensing a nitrato alkanoic acid with a sulfur-containing amino acid or peptide, which prevent nitrate tolerance or overcome existing tolerance and which are useful for the treatment of cardiac diseases including circulatory diseases, high blood pressure, cardiac insufficiency and for dilating the peripheral vessels.

18 Claims, 8 Drawing Sheets

ISM-5  
mean ± sem. N=3

5.12 mg/kg p.o. in Ethanol

ISM-5
mean ± sem. N=3

5.12 mg/kg p.o. in Ethanol

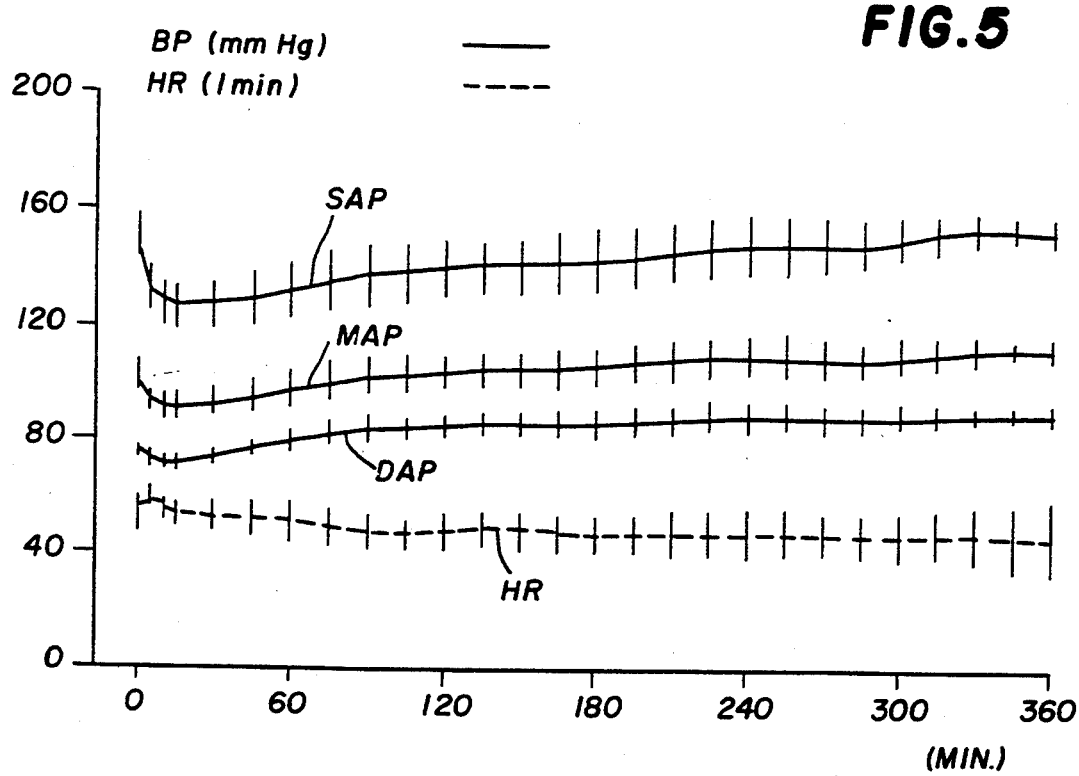
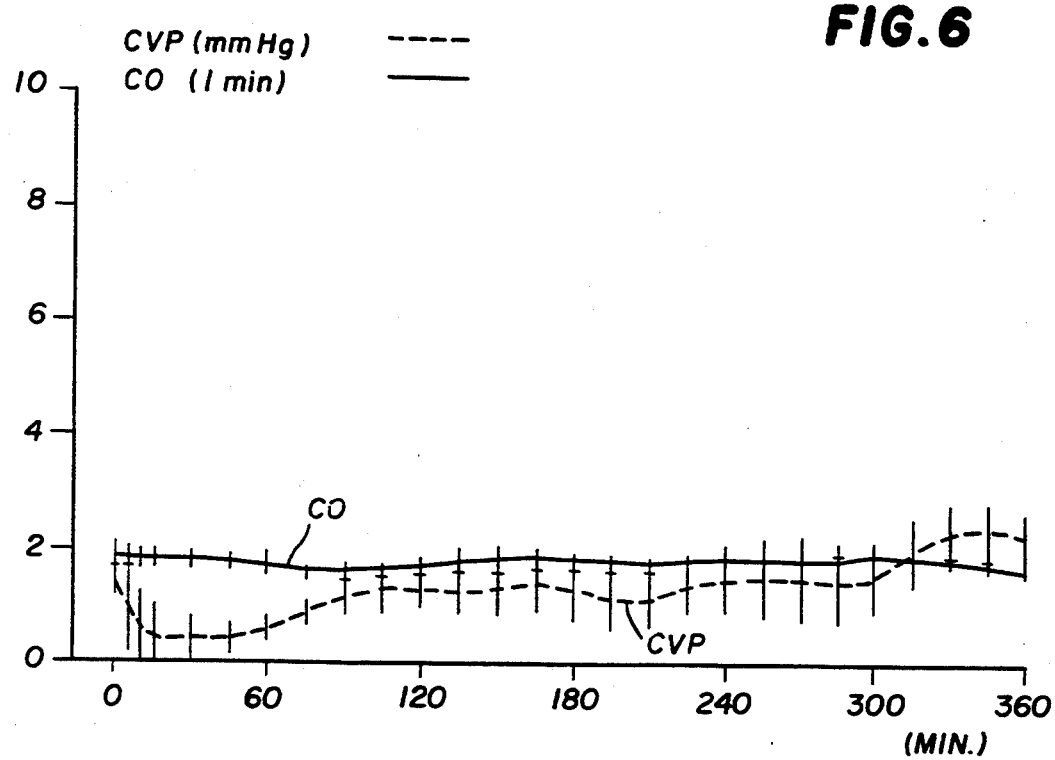
ISM-5           5.12 mg/kg i.v. in NaCl 0.9%
mean ± sem. N=3

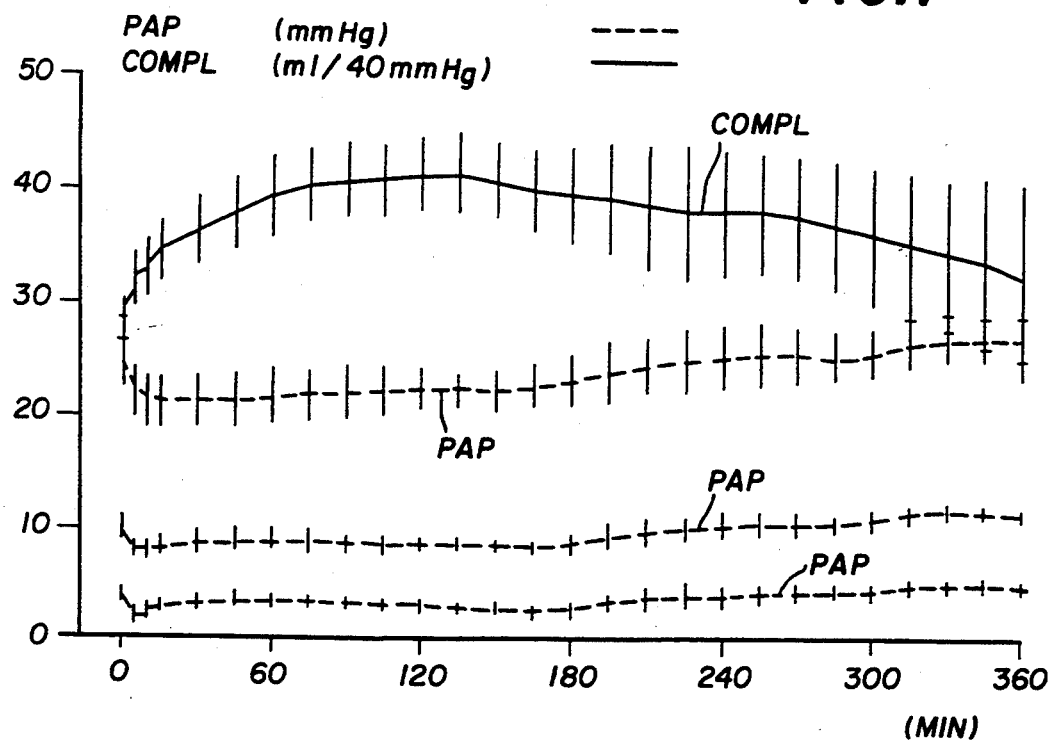
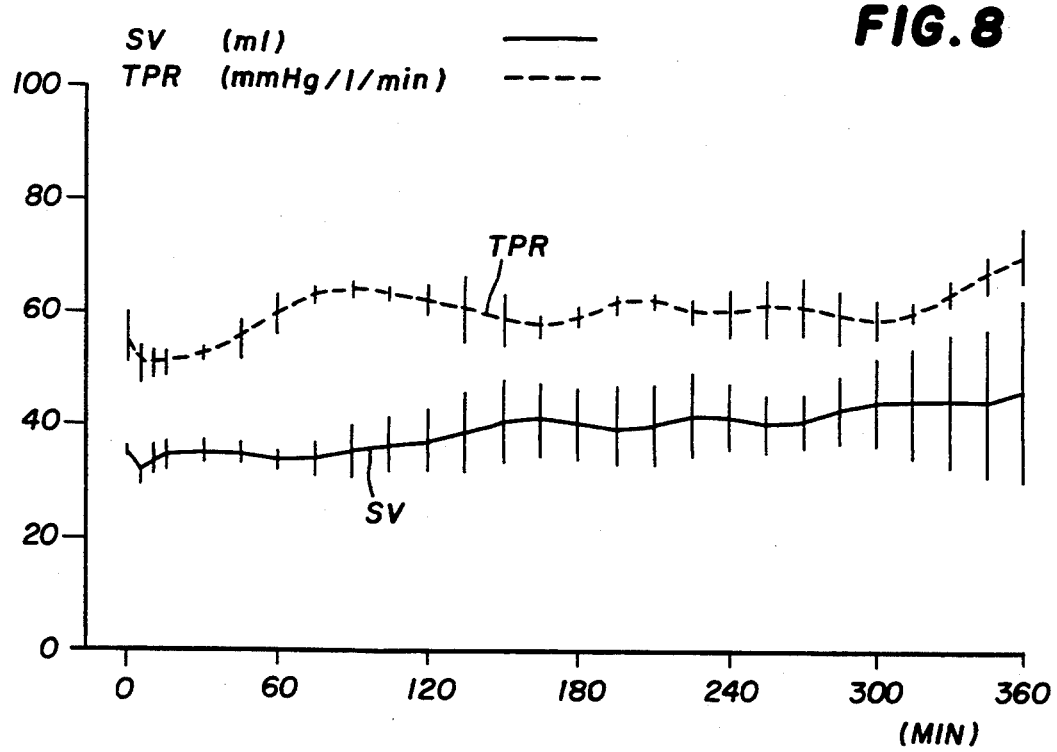

Nitroxy-Piv-Meth-Et.
mean ± sem. N=5

8.63 mg/kg i.v. in DMSO 100%

Nitroxy-Piv-Meth-Et.    8.63 mg/kg i.v. in DMSO 100%
mean ± sem. N=5

Nitroxy-Piv-Meth-Et.
mean ± sem. N=5

8.63 mg/kg p.o. in DMSO 100%

Nitroxy-Piv-Meth-Et.
mean ± sem. N=5

8.63 mg/kg p.o. in DMSO 100%

ORGANIC NITRATES AND METHOD FOR THEIR PREPARATION

This is a continuation of U.S. application Ser. No. 07/818,502, filed Jan. 8, 1992, now abandoned, in turn a C-I-P of Ser. No. 07/406,165, filed Sep. 12, 1989, now abandoned.

This invention is concerned with new organic nitrates and with a method for their preparation.

BACKGROUND OF THE INVENTION

Organic nitrates (nitric acid esters) have been proven useful in the therapy of cardiac diseases.

They act both by alleviating the before and after effects of a load on the heart, as well as through improvement of the oxygen supply to the heart by dilation of the coronary vessels.

In any case, it has been found in recent years that the organic nitrates which have been used so far in therapy, such as glycerol trinitrate (GTN), isosorbid-5-mononitrate or isosorbid dinitrate, because of nitrate tolerance, exhibit a clear drop in efficacy in a relatively short time when continuous high dosages are administered to the patient. Numerous experiments indicate that the presence of sulfhydryl (—SH) groups prevents the development of nitrate tolerance and that an existing tolerance can be reduced.

The development of tolerance is presently understood to be as follows:

According to the present state of knowledge, the pharmacological action of organic nitrate compounds depends on the presence of cysteine. The organic nitrate forms a common precursor with cysteine and, when it decomposes, —NO radicals among others, are liberated and activate soluble guanylate cyclase, the target enzyme, of the smooth muscle cells. Subsequent reactions triggered by the formation of cGMP lead to relaxation or dilation of the vessels.

The reactive and short-lived, and so far, only hypothetical intermediate product would have to be a thioester of nitric acid or a thionitrate. Through intramolecular rearrangement and other subsequent reactions which have not yet been established, the final formation of a nitroso thiol is postulated, from which nitrogen monoxide or nitrite ions are liberated. On the other hand, the enzyme-dependent degradation with the aid of GSH reductase would not be of significance for the pharmacological action, because it leads exclusively to the formation of nitrite ions. As already stated, the non-enzymatic degradation needs cysteine and can thus be exhausted in a dose-dependent manner (exhaustion of the SH group pool), so that over a long term sufficient NO, which is the actual activator of guanyl cyclase, can no longer be formed so that the clinical effectiveness will be reduced.

SUMMARY OF THE INVENTION

The compounds provided by the invention for the therapy of cardiac diseases have a specific structure which includes a group from a nitrato fatty acid (nitratoalkanoic acid) and a group from a sulfur-containing amino acid or peptide.

Therefore, an object of the present invention is to provide new organic nitrates which, based on the general structural principle that they include a sulfhydryl group, are characterized by the fact that they prevent or resist development of nitrate tolerance and/or reverse existing nitrate tolerance when used for the therapy of cardiac diseases.

DETAILED DESCRIPTION OF THE INVENTION

This object is achieved by the fact that compounds are provided having the general formula:

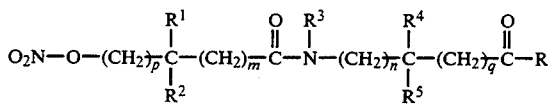

wherein the symbols have the following meaning:
R represents hydroxy, a lower alkoxy, a lower alkenoxy, a di-lower alkylamino-lower alkoxy, acylamino-lower alkoxy, acyloxy-lower alkoxy, aryloxy, aryl-lower alkoxy, substituted aryloxy or substituted aryl lower alkoxy groups, where the substituent is methyl, methoxy or a halogen such as chloro, bromo or fluoro; amino, lower alkylamino, di-lower alkylamino, aryl-lower alkylamino, hydroxy-lower alkylamino or amino acid residues as present in peptide bonds, $R^1$ represents hydrogen, an alkyl having 1 to 6 carbon atoms, a substituted lower alkyl in which the substituent is a halogen, groups defined by R containing hydroxy, lower alkoxy, aryloxy, amino, lower alkylamino, furthermore acylamino, acyloxy, arylamino, mercapto, lower alkylthio or arylthio, $R^2$ represents hydrogen, lower alkyl and the additional groups represented by $R^1$, $R^3$ represents hydrogen or lower alkyl, $R^4$ represents hydrogen, lower alkyl, phenyl, methoxy phenyl, phenyl-lower alkyl, methoxyphenyl-lower alkyl, hydroxyphenyl-lower alkyl, hydroxy-lower alkyl, alkoxy-lower alkyl, amino-lower alkyl, acylamino-lower alkyl, mercapto-lower alkyl or lower alkylthio-lower alkyl, $R^5$ represents lower alkyl thiol, —SH, S—acyl and particularly —S-acetyl, —S-propionyl, —S-butyryl, —S-isobutyryl, —S-capryl, —S-pivaloyl and —S-benzoyl;

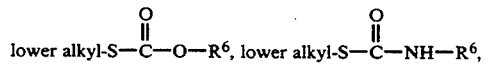

and lower alkylthio-lower alkanoic acid and esters and amides thereof, and lower alkylthio-lower alkyl, wherein $R^6$ represents hydrogen and lower alkyl groups in which R and $R^5$ are bonded together and form part of a thiolactone group, groups in which R and $R^4$ are bonded together in the form of an ester or amide, groups in which $R^3$ and $R^4$ are bonded together in the form of an alkylene bridge with 2 to 4 carbon atoms, an alkylene bridge with 2 to 3 carbon atoms and a sulfur atom, an alkylene bridge with 3 to 4 carbon atoms, which contains a double bond or an alkylene bridge as above, which can be substituted by one or more hydroxy, lower alkoxy, lower alkyl or di-lower alkyl groups, m, n and q are whole numbers or integers from 0 to 10, desirably 0 to 3, p is 0 or 1, and pharmaceutically acceptable salts thereof.

According to a further feature of the invention, the nitrato alkanoic acid components can have a chain length of $C_2$-$C_6$, they may be straight-chain or branched chain, and they may be racemic or optical isomers.

Preferably, the amino acids cysteine, methionine or homocysteine are used in making the organic nitrates so that groups from such amino acids are present therein.

Advantageously, the amino acids are of the stereochemical L-form.

Cysteine and/or methionine are desirably present in the form of their methyl, ethyl or propyl esters.

The —SH group of cysteine can be esterified with a lower alkanoic acid having 2 to 8 carbon atoms.

According to an especially advantageous further development the invention provides compounds having the following chemical names:

N-(2-nitratoacetyl)-cysteine ethyl ester
N-(2-nitratoacetyl)-S-acetyl-cysteine ethyl ester
N-(2-nitratoacetyl)-S-propionyl-cysteine ethyl ester
N-(2-nitratoacetyl)-S-pivaloyl-cysteine ethyl ester
N-(2-nitratoacetyl)-methionine methyl ester
N-(2-nitratopropionyl)-cysteine
N-(2-nitratopropionyl)-cysteine ethyl ester
N-(2-nitratopropionyl)-methionine ethyl ester
N-(2-nitratobutyryl)-cysteine
N-(2-nitratobutyryl)-cysteine ethyl ester
N-(2-nitratobutyryl)-S-acetyl-cysteine ethyl ester
N-(2-nitratobutyryl)-S-butyryl-cysteine ethyl ester
N-(2-nitratobutyryl)-methionine ethyl ester
N-(2-nitratoisobutyryl)-cysteine
N-(2-nitratoisobutyryl)-cysteine ethyl ester
N-(2-nitratoisobutyryl)-S-benzoyl-cysteine ethyl ester
N-(2-nitratoisobutyryl)-S-acetyl-cysteine ethyl ester
N-(2-nitratoisobutyryl)-S-pivaloyl-cysteine ethyl ester
N-(2-nitratoisobutyryl)-methionine ethyl ester
N-(3-nitratobutyryl)-cysteine
N-(3-nitratobutyryl)-cysteine ethyl ester
N-(3-nitratobutyryl)-S-acetyl-cysteine ethyl ester
N-(3-nitratobutyryl)-S-propionyl-cysteine ethyl ester
N-(3-nitratobutyryl)-methionine ethyl ester
N-(3-nitratobutyryl)-homocysteine thiolactone
N-(3-nitratopivaloyl)-cysteine
N-(3-nitratopivaloyl)-cysteine ethyl ester
N-(3-nitratopivaloyl)-cysteine ethyl ester-S-ethyl carbonate
N-(3-nitratopivaloyl)-S-acetyl-cysteine ethyl ester
N-(3-nitratopivaloyl)-S-propionyl-cysteine ethyl ester
N-(3-nitratopivaloyl)-S-butyryl-cysteine ethyl ester
N-(3-nitratopivaloyl)-S-isobutyryl-cysteine ethyl ester
N-(3-nitratopivaloyl)-S-pivaloyl-cysteine ethyl ester
N-(3-nitratopivaloyl)-S-benzoyl-cysteine ethyl ester
N-(3-nitratopivaloyl)-methionine ethyl ester
N-(3-nitratopivaloyl)-methionine
N-(3-nitratopivaloyl)-homocysteine thiolactone
N-(2-nitratohexanoyl)-cysteine ethyl ester
N-(2-nitratohexanoyl)-S-propionyl-cysteine ethyl ester
N-(3-nitratohexanoyl)-cysteine ethyl ester
N-(3-nitratohexanoyl)-methionine methyl ester
N-(12-nitratolauroyl)-cysteine
N-(12-nitratolauroyl)-cysteine ethyl ester
N-(12-nitratolauroyl)-S-acetyl-cysteine
N-(12-nitratolauroyl)-S-pivaloyl-cysteine
and other esters thereof, particularly lower alkyl esters such as the methyl, propyl, isopropyl, butyl and pentyl esters.

According to another aspect of the invention, drugs or medicines containing one or more of the compounds are provided.

The compounds provided by this invention can be administered to a patient as pure esterified or non-esterified compounds, or in the form of nontoxic acid addition salts, orally or intravenously. The patient may be a human or a lower animal. To obtain a practical size to dosage relationship one or more of the compounds may be combined with a suitable pharmaceutical carrier and made into unit-dosage forms for administration to a patient.

Pharmaceutical carriers which are liquid or solid can be used. The preferred liquid carriers are water, ethanol, propyleneglycol, polyethyleneglycol and mixtures thereof. Flavoring materials can be included in the solutions as desired. A solution for intravenous injection may contain about 1 to 40 mg of active compound per liter.

Solid pharmaceutical carriers such as starch, sugar and talc can be used to form powders. The powders can be used as such or be tableted, or be used to fill gelatin capsules. Suitable lubricants like magnesium stearate, binders such as gelatin and disintergrating agents like sodium carbonate in combination with citric acid can be used to form the tablets.

Unit dosage forms such as tablets and capsules can contain any suitable predetermined amount of one or more of the compounds and can be administered one or more at a time at regular intervals. Such forms, however, may contain a concentration of about 0.1 to 10% by weight of a compound of this invention.

A typical tablet can have the composition:

|  | Mg. |
| --- | --- |
| 1. N-(3-nitrato-S-pivaloyl)-cysteine ethyl ester | 25 |
| 2. Starch, U.S.P. | 57 |
| 3. Lactose, U.S.P. | 73 |
| 4. Talc, U.S.P. | 9 |
| 5. Stearic acid | 6 |

Powders 1, 2 and 3 are slugged, then granulated, mixed with 4 and 5, and tableted.

Daily administration of about 1 to 500 mg, and preferably about 10 to 200 mg, of N-(3-nitrato-S-pivaloyl)-cysteine ethyl ester and other compounds of this invention, including those disclosed and named above, is usually satisfactory. However, since some variation between compounds is to be expected, the precise dosages of each is to be evaluated prior to administration. Furthermore, the differences in patients normally will require prescription of various amounts of the active drugs from case to case. In general, treatment may be achieved with the administration of unit dosage forms containing about 1 to 50 mg. of the active compound administered during a day. The usual unit dosage may be about 10 to 30 mg. administered one to three times a day.

These organic nitrates, desirably in the form of a pharmaceutical composition, can be used for the treatment of cardiac disease as manifested by circulatory diseases, for example, as coronary dilators, as agents for the treatment of high blood pressure, cardiac insufficiency and for dilating the peripheral vessels, including the vessels of the brain and kidneys.

Finally, the compounds can be prepared by condensing the corresponding nitrato fatty acids or their reactive derivatives with the amino group of an amino acid or a peptide. If desired, the compounds obtained can be subjected to side-chain alkylation or side-chain acylation in a subsequent reaction step.

The process thus comprises reacting a compound of the formula:

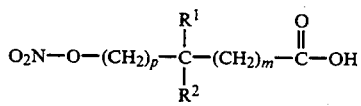

in the form of a member of the group consisting of the free acid, a reactive halide, azide, ester and anhydride, with a compound of the formula

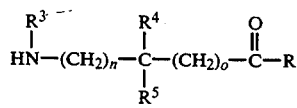

to produce a compound of the formula

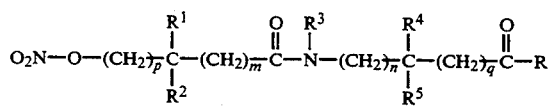

wherein R, $R^1$, $R^2$, $R^3$, $R^4$, $R^5$, m, n, o and p have the meaning previously set forth herein.

Reactive derivatives of the nitrato fatty acids which can be used as reactants according to the invention are, for example, acid halides, acid anhydrides, activated amides and activated esters. Preferably, acid chlorides, acid azides, symmetrical acid anhydrides, activated esters and mixed anhydrides with organic or inorganic acids can be used.

The condensation reaction of a nitrato fatty acid with an amino group of an amino acid can also be carried out in an inert solvent and in the presence of a condensing agent which promotes the formation of an acid amide bond, a carbodiimide such as N,N'-dicyclohexyl carbodiimide or a similar carbodiimide, an imine compound such as diphenylketene-N-cyclohexylimine or pentamethylene-ketene-N-cyclohexylimine, or a phosphate or phosphite such as triethyl phosphite, ethyl polyphosphate or isopropyl polyphosphate, over a period of 1–48 hours at temperatures from −10° C. to the refluxing temperature of the solvent used.

The following examples illustrate without limiting the invention.

Example 1

Preparation of N-(3-nitratobutyryl)cysteine ethyl ester

First Step

Saponification of 3-hydroxybutyric acid ethyl ester
3-Hydroxybutyric acid ethyl ester (Aldrich), 13.2 g (0.1 mole), was reacted with 4.0 g (0.1 mole) of NaOH dissolved in 100 ml of water. The reaction was complete when the solution became homogeneous.

The reaction mixture was acidified with 10 ml of concentrated HCl and then extracted twice using 100 ml of ethyl acetate each time. Then the solution was evaporated on a rotary evaporator; a thin flowing oil remained.

The yield was 8.81 g (theory: 10.4 g) of 3-hydroxybutyric acid.

Second Step

Nitration of the 3-hydroxybutyric acid
3-Hydroxybutyric acid, 8.81 g (0.08 mole), and 50 mg of urea were dissolved in 50 ml of acetic acid at 5° C. First 6.27 ml (0.15 mole) of $HNO_3$ was added dropwise and then 14.17 ml (0.15 mole) of $Ac_2O$ was added under cooling. The reaction mixture was stirred overnight.

The mixture was worked up by adding 200 ml of ice water to the solution obtained and then extracting it with ethyl acetate. The organic phase was then extracted with $NaHCO_3$. The $NaHCO_3$ phase was acidified with concentrated HCl and extracted with ethyl acetate. Finally, the solution was evaporated on a rotary evaporator, whereupon a thin flowing oil remained.

The yield was 9.4 g (theory 11.9 g) of 3-nitratobutyric acid.

Third Step

Preparation of N-(3-nitratobutyryl)-cysteine ethyl ester
3-Nitratobutyric acid, 16.6 g (0.11 mole), was dissolved in 100 ml of dichloromethane. While passing $N_2$ through the mixture, 17.9 g (0.12) of cysteine ethyl ester was added slowly at 15° C. Then 24.7 g (0.12 mole) of dicyclohexyl carbodiimide (DCC) dissolved in 80 ml of dichloromethane was added dropwise slowly at 15° C. while $N_2$ was passed through. The dicyclohexylurea formed was filtered off at the end of the reaction under suction and the solution was washed with 150 ml of 0.1N HCl. Then the solution was evaporated on a rotary evaporator.

A purified sample of the substance was prepared by column chromatography and recrystallization from ethanol/n-hexane.

Yield: 6.88 g (theory: 30.83 g) M.p. 77.8° C.

Example 2

Preparation of N-(3-nitratobutyryl)-methionine ethyl ester
3-Nitratobutyric acid, 6.35 g (0.043 mole), 7.47 g (0.043 mole) of methionine ethyl ester and an amount of dimethylaminopyridine (DMAP), that the tip of a spatula holds, were dissolved in 100 ml of dichloromethane with stirring and cooling to 10° C. Then 10.31 g (0.05 mole) of DCC was dissolved in 80 ml of $CH_2Cl_2$ and added dropwise slowly under simultaneous introduction of nitrogen. After the reaction was completed, the solution was filtered off under suction, washed with $NaHCO_3$ and finally with HCl. The solution was evaporated in a rotary evaporator, whereupon an oil remained.

Purification of a sample was carried out by column chromatography or by crystallization in the cold.

The yield was 1.95 g (theory 12.05 g) of N-(3-nitratobutyryl)-methionine ethyl ester as a colorless oil.

Example 3

Preparation of N-(3-nitratopivaloyl)-cysteine ethyl ester

First Step

Preparation of nitratopivalic acid methyl ester
Hydroxypivalic acid methyl ester, 25.0 g (0.19 mole) and 0.12 g of urea were dissolved at room temperature in 250 ml of $CH_2Cl_2$ and cooled to 5° C. under stirring. Then 23.8 g (0.38 mole) of $HNO_3$ (100%) was added dropwise with stirring, so that the temperature did not exceed 10° C. The mixture was cooled to 5° C. and 38.6 g (0.38 mole) of acetic anhydride was added dropwise with stirring in such a way that the temperature did not exceed 10° C., the mixture was then stirred into an ice bath with cooling for a 15 minute period and then slowly warmed to room temperature and further stirred overnight at room temperature. The batch was introduced slowly into 500 ml of ice water under stirring. The $CH_2Cl_2$ phase was separated and was washed once with each of 100 ml of distilled $H_2O$, 100 ml of saturated aqueous $NaHCO_3$ solution and again with 100 ml of distilled $H_2O$. Then the $CH_2Cl_2$ extract was evaporated to dryness on a Rotavapor at a maximum bath temperature of 40° C. in the vacuum of a water jet pump. The light-yellow oily residue distilled at the vacuum of an oil pump at a bath temperature of 60° C. as a clear thin flowing oil.

Yield: 31.5 g, corresponding to 94.0% of theory

Second Step

Preparation of nitratopivalic acid

NaOH, 14.0 g (0.350 mole), was dissolved in $H_2O$ and cooled to about 10° C. Then a solution of 31.0 g (0.175 mole) of nitratopivalic acid methyl ester in 250 ml of methanol was added with stirring whereupon the reaction mixture developed a yellow color and the temperature increased to about 25° C. After 90 minutes of stirring, the batch was neutralized with 29.5 ml (0.35 mole) of 37% HCl and the methanol was completely distilled off in a Rotavapor. The aqueous phase was extracted twice using 200 ml of methylene chloride each time. The combined methylene chloride extracts were washed once with 50 ml of distilled $H_2O$ and the methylene chloride phase was evaporated to dryness on the Rotavapor. The colorless, oily residue was dissolved in 100 ml of ethyl acetate and again evaporated to dryness on the Rotavapor, whereupon a white solid residue remained from which the solvent residues were removed at the vacuum of an oil pump (0.4 torr) at a bath temperature of about 40° C. over a period of 15 minutes in a Rotavapor. The solid, white residue of 25.44 g (89.1% of theory) was dissolved in 100 ml of boiling n-hexane and 2 ml of diisopropyl ether was added. After cooling to room temperature and addition of nucleating crystals, the product crystallized out. The product was allowed to stand at 0° C. for 72 hours, the crystals were filtered off under suction and, after washing twice using 10 ml of n-hexane each time, it was dried in a vacuum drying oven to a constant weight at room temperature at about 2 torr.

M.p. 54.2° C. Yield: 23.66 g, corresponding to 82.9% of the theory

Third Step

Preparation of N-(3-nitratopivaloyl)-cysteine ethyl ester

L-cysteine ethyl ester base, 10.7 g (71.7 mmoles), was dissolved in 200 ml of methylene chloride at room temperature under stirring in an $N_2$ atmosphere. Then 11.4 g (70.0 mmoles) of crystalline nitratopivalic acid were added and dissolved under stirring at room temperature. Then a solution of 14.8 g (71.7 mmoles) of N,N-dicyclohexylurea (DCC) in 50 ml of methylene chloride was added to this mixture with stirring in a nitrogen atmosphere at room temperature. The addition was carried out dropwise over a period of about 15 minutes whereupon the temperature increased to 35° C. After further stirring, white dicyclohexylurea precipitated. The batch was cooled to room temperature and stirred overnight under a nitrogen atmosphere. The dicyclohexylurea was then filtered off through a sintered glass filter and was washed once with 50 ml of $CH_2Cl_2$. The combined methylene chloride solutions were washed once with 100 ml of 1N HCl and twice using 100 ml of distilled $H_2O$ each time (under an $N_2$ atmosphere) and then evaporated in a Rotavapor at a bath temperature of about 40° C. in the vacuum of a water jet pump at an initial pressure of 550 mbar to approximately 20 mbar. A yellow-brown oil was obtained.

Yield: 21.2 g, corresponding to 102.9% of theory.

The substance was purified by recrystallization from ethanol/hexane in the cold.

Yield: 13.42 g of N-(3-nitratopivaloyl)-cysteine ethyl ester as a light-pink oil, corresponding to 65.1% of theory.

Fourth Step

Preparation of N-(3-nitratopivaloyl)-S-acetyl-cysteine ethyl ester

To 10.3 g (35.0 mmoles) of N-(3-nitratopivaloyl)cysteine ethyl ester dissolved in 70 ml of dichloromethane was added a solution of 4.3 g (42.0 mmoles) of acetic anhydride in 10 ml of dichloromethane in the cold dropwise with stirring. Then a solution of 5.0 g (49.0 mmoles) of triethylamine in 20 ml of dichloromethane was added dropwise in the cold with stirring. After the end the reaction, the batch was washed with 1N HCl, 10% aqueous sodium bicarbonate solution and water. The dichloromethane extract was evaporated to dryness on the Rotavapor. 11.6 grams of a light-yellow, oily product thus was obtained from which 7.8 g of crystalline product (66.3% of theory) was obtained by recrystallization from ethanol/water in the cold and with the addition of nucleating crystals.

M.p. <5° C.

Fourth Step/Variation 1

Preparation of N-(3-nitratopivaloyl)-S-butyryl-cysteine ethyl ester

If one uses 6.7 g (42.0 mmoles) of butyric acid anhydride instead of acetic anhydride as described in Step 4, and if the reaction and the work-up is conducted in the same way, 13.0 g of a light-yellow, oily product is obtained from which 9.7 g of crystalline product (corresponding to 76.2% of theory) was obtained by recrystallization in the cold, as described in Step 4.

M.p.:<5° C.

Fourth Step, Variation 2

Preparation of N-(3-nitratopivaloyl)-S-pivaloyl-cysteine ethyl ester

If one uses 7.8 g (42.0 mmoles) of pivalic acid anhydride instead of the acetic anhydride described in Step 4, and if one conducts the reaction and the work-up in the same way, 14.1 g of a light-yellow, oily product is obtained from which one obtains 10.5 g of crystalline product (corresponding to 79.5% of theory) by recrystallization as described in Step 4.

M.p. 45° C.

Fourth Step/Variation, 3

Preparation of N-(3-nitratopivaloyl)-cysteine ethyl ester-S-ethyl carbonate

If one uses 4.3 g (42.0 mmoles) of ethyl chloroformate instead of the acetic anhydride described in Step 4, and if one conducts the reaction and the work-up in the same way, 11.5 g of a light-yellow, oily product is obtained from which one obtains 9.5 g of crystalline product (corresponding to 74.1% of theory) by recrystallization as described in Step 4.

M.p. 36° C.

Example 4

Preparation of N-(3-nitratopivaloyl)-methionine ethyl ester

L-methionine ethyl ester base, 12.4 g (70.0 mmoles), was dissolved in 250 ml of methylene chloride at room temperature in an $N_2$ atmosphere. Then 11.4 g (70.0 mmoles) of crystalline nitratopivalic acid was added and dissolved with stirring at room temperature. To the mixture was added dropwise a solution of 14.8 g (71.7 mmoles) of N,N-dicyclohexylurea (DCC) in 50 ml of methylene chloride in about 15 minutes at room temperature under stirring and in a nitrogen atmosphere, whereupon the temperature increased to 35° C. After further stirring, white dicyclohexylurea precipitated. The batch was cooled to room temperature and was stirred overnight in a nitrogen atmosphere. The DCC urea was then filtered off through a sintered glass filter and was washed once with 50 ml of $CH_2Cl_2$. The combined methylene chloride solutions were washed once with 100 ml of 1N HCl and twice with 100 ml of distilled $H_2O$ each time (under an $N_2$ atmosphere) and then evaporated in the Rotavapor at a bath temperature of about 40° C. and in the vacuum of a water jet pump at an initial pressure of 550 mbar, which went to about 20 mbar. A light-yellow oil was obtained.

Yield: 24.9 g of crude N-(3-nitratopivaloyl-L-methionine methyl ester, corresponding to 110.3% of theory.

The crude product was purified by sample chromatography on a column.

Yield: 17.6 g of N-(3-nitratopivaloyl)-methionine ethyl ester as a colorless oil, corresponding to 78.0% of theory.

Example 5

N-(12-nitratolauroyl)-S-acetyl-cysteine

First Step

Preparation of 12-nitratolauric acid

12-Hydroxylauric acid, 54.1 g (0.250 mole), and 0.3 g of urea were dissolved in 1.3 liter of $CHI_3$ with slight warming and then cooled to 20° C. with stirring. Then, with stirring, 23.6 g (0.375 mole) of $HNO_3$ (100%) was added slowly, dropwise, whereupon the temperature rose to 27° C. The mixture was cooled to 20° C. and 38.3 g (0.375 mole) of acetic acid anhydride was added dropwise under stirring and cooling, whereby a temperature limit of 25° C. was observed. The mixture was stirred overnight at room temperature. Finally, it was washed five times using 0.5 liter of distilled $H_2O$ each time. The $CHCl_3$ phase, which had been dried over $Na2SO_4$ and clarified with pulverized activated carbon, was evaporated to dryness in a Rotavapor at a bath temperature of 50° C. at the vacuum of a water jet pump. The oily residue of 60.8 g was dissolved in 500 ml of boiling n-hexane and, after cooling to room temperature, it was allowed to stand overnight in a refrigerator at 0° C. The crystalline product was precipitated and was washed twice using 50 ml of n-hexane each time. Finally, the product was evaporated to constant weight in a vacuum drying oven at room temperature and at about 2 torr.

M.p. 29° C.

Yield: 39.4 g, corresponding to 60.3% of theory.

Second Step

Preparation of 12-nitratolauric acid chloride

Nitratolauric acid, 2.61 g (10 mmoles), was dissolved in 50 ml of methylene chloride and 4.44 g (35 mmoles) of oxyalyl chloride in 50 ml of methylene chloride was added dropwise at room temperature with stirring. The mixture was stirred overnight. Finally, the product was evaporated to dryness in a rotary evaporator.

Yield: 3 g, corresponding to 93.2% of theory.

Third Step

Preparation of N-(12-nitratolaurol)-cysteine

Under a nitrogen atmosphere, 6.06 g (50 mmoles) of L-cysteine was introduced into 300 ml of DMF with stirring. Then 5.60 g (20 mmoles) of 12-nitratolauric acid chloride in 50 ml of dichloromethane was added dropwise. Since a clear solution was not obtained, the mixture was heated to 60° C. Finally, 100 ml of distilled $H_2O$ was added and the mixture was stirred overnight at room temperature. Finally, the mixture was diluted with 300 ml of $H_2O$ and was extracted four times using 200 ml of ethyl acetate each time. The organic phase was dried over $Na_2SO_4$ and then evaporated. The residue was taken up in 100 ml of ether and was allowed to stand in a refrigerator overnight at 0° C. White crystals were obtained.

M.p. 74°–75° C.

Yield: 4.1 g of N-(12-nitratolauroyl)-cysteine.

Fourth Step

Preparation of N-(12-nitratolauroyl)-S-acetyl-cysteine

Under a nitrogen atmosphere, 1.82 g (5 mmoles) of N-(12-nitratolauroyl)-cysteine was placed in 20 ml of ethyl acetate. The mixture was cooled to 0° C. and 2.5 ml of acetic anhydride was added dropwise. Then at −5° C., 1.52 g (15 mmoles) of triethylamine dissolved in 5 ml of ethyl acetate was added dropwise. The reaction solution was washed with water and evaporated to dryness.

M.p.: oil at room temperature.

Yield: 2 g, corresponding to 98.4% of theory.

Example 6

Preparation of N-(12-nitratolauroyl)-cysteine ethyl ester

Cysteine ethyl ester base, 4 g (26.8 mmoles), was dissolved in 50 ml of methylene chloride and 2.8 g (10 mmoles) of 12-nitratolauric acid chloride dissolved in 50 ml of methylene chloride was added dropwise with stirring and the mixture then was stirred overnight. The precipitated cysteine ethyl ester HCl salt was filtered off under suction and the solvent was removed in a Rotavapor. The oily residue (6 g) was dissolved in 100 ml of ether and was allowed to stand in a refrigerator overnight at 0° C. The precipitated product was filtered off.

M.p. 59°–60° C.

Yield: 1.6 g, corresponding to 40.0% of theory.

Example 7

Preparation of N-(2-nitratopropionyl)-cysteine ethyl ester

First Step

Preparation of nitratolactic acid ethyl ester

Lactic acid ethyl ester, 33 g (0.28 mole), was dissolved in 300 ml of dichloromethane. After addition of 100 mg of urea, 22.5 ml (0.56 mole) of 100% nitric acid was added dropwise at a temperature of 5°–10° C. The solution was cooled to 0° C. Then 52.8 ml (0.56 mole) of acetic anhydride was added dropwise in such a way that the temperature did not rise above 5° C. The solution was allowed to stand overnight at room temperature and then was washed with 250 ml of water. The organic phase was separated and dried over sodium sulfate. After filtration, the dichloromethane was distilled off. The oily residue obtained was processed by distillation.

Yield: 30.34 g, corresponding to 66.4% of theory.
B.p.: 34° C. (0.25 torr).

Second Step

Preparation of nitratolactic acid

Nitratolactic acid ethyl ester, 30 g (0.18 mole), was dissolved in 80 ml of dioxane. Then 30 ml of water and 2 g (0.02 mole) of sulfuric acid were added to the solution and the mixture was refluxed for 19 hours. The solution was evaporated to a volume of about 50 ml and then diluted with 300 ml of water. The pH value was adjusted to 7–8 by the addition of sodium bicarbonate. The unreacted ester was removed by extraction with dichloromethane.

The aqueous phase was adjusted to pH 1 with concentrated hydrochloric acid and extracted three times using 150 ml of ethyl acetate each time. The extracts were combined and dried over sodium sulfate. After filtration the ethyl acetate was removed completely in a rotary evaporator.

Yield: 14.6 g of colorless oil, corresponding to 59.2% of theory.

Third Step

Preparation of N-(2-nitratopropionyl)-cysteine ethyl ester

In a nitrogen atmosphere, 17 g (0.13 mole) of nitratolactic acid and 18.9 g (0.13 mole) of cysteine ethyl ester were dissolved in 200 ml of dichloromethane at 10°–15° C. At 15°–20° C. a solution of 28.6 g (0.14 mole) of N,N-dicyclohexyl carbodiimide and 75 ml of dichloromethane was added dropwise. After 1 hour, the precipitated N,N-dicyclohexylurea was filtered off and was washed with 75 ml of dichloromethane. The filtrate was extracted twice using 50 ml of 0.1N hydrochloric acid each time. The organic phase was evaporated completely on a rotary evaporator. The crude crystalline product (22.4 g) was recrystallized from 100 ml of ethanol/n-hexane (1:1).

Yield: 7.6 g, corresponding to 22.6% of theory.
M.p.: 92.8° C.

EXAMPLE 8

Preparation of N-(3-Nitratohexanoyl)-L-cysteine ethyl ester 5.1 g of 3-nitratohexanoic acid, 5.94 g of cysteine ethyl ester hydrochloride, and a catalytic amount of dimethylaminopyridine were suspended in 50 ml of dioxan. At room temperature a solution of 6.58 g of N,N-dicyclohexylcarbodiimide in 20 ml of dioxan was added dropwise. The batch was stirred for two days at room temperature and then filtered. The dioxan was evaporated, the residue was dissolved in 100 ml of ethylacetate and extracted twice with 100 ml aliquots of 0.1N HCl. Then the solution was evaporated on a rotary evaporator. Yield: 4.6 g (51.44% of theory) of the product as a light brown oily product.

EXAMPLE 9

Preparation of N-(3-Nitratopivaloyl)-homocysteine thiolactone 5 g of 3-nitratopivalic acid and 4.7 g of homocysteine thiolactone HCl were suspended in 50 ml of tetrahydrofuran. After the addition of 2.4 g of pyridine, at a temperature of 5°–10° C., a solution of 6.2 g of N,N-dicyclohexylcarbodiimide in 20 ml of tetrahydrofuran was added dropwise. The mixture was stirred overnight at room temperature and then filtered. The filtrate was evaporated on a rotary evaporator. 150 ml of 1N NaOH were added and extracted twice with 100 ml aliquots of $CH_2Cl_2$. The organic phase was washed with 100 ml of 1N HCl and evaporated on a rotary evaporator. Yield: 2.6 g of oil. The product was crystallized from 20 ml of a mixture of n-hexane and 10 ml of ethanol. Yield: 510 mg (6.5% of theory). M.p.: 88.6°

EXAMPLE 10

Preparation of N-(2-Nitratoacetyl)-L-cysteine ethyl ester 12.6 g of cysteine ethyl ester was dissolved in a solution of 11.35 g of 2-nitratoacetic acid in 200 ml of ethyl acetate. At a temperature of 20°–25° C., a solution of 19.4 g of N,N-dicyclohexylcarbodiimide in 20 ml of $CH_2Cl_2$ was added dropwise. The mixture was stirred overnight at room temperature and filtered. The filtrate was evaporated on a rotary evaporator. Yield: 17.9 g. The product was recrystallized twice from isopropanol. Yield: 2.5 g (11.66% of theory). M.p.: 76.1° C.

EXAMPLE 11

Preparation of N-(3-Nitratopivaloyl)-S-propionyl-L-cysteine ethyl ester

N-(3-nitratopivaloyl)-cysteine ethyl ester (10.3 g) and 5.5 g of propionic anhydride are combined in 60 ml of dichloromethane at room temperature in a nitrogen atmosphere with stirring. Then 5 g of triethylamine in dichloromethane is added dropwise under stirring. After the end of the reaction, the solution is washed with 1N HCl, 10% aqueous sodium bicarbonate solution and water. The dichloromethane extract is evaporated to dryness on a rotavapor. 12.46 grams (101.6% of theory) of a light brown oily product is obtained. The identity of the product is verified by mass spectroscopy.

EXAMPLE 12

Preparation of N-(2-Nitratohexanoyl)-cysteine ethyl ester 2.74 g of 2-nitratohexanoic acid, 2.78 g of cysteine ethyl ester HCl and a catalytic amount of dimethylaminopyridine were dissolved in 50 ml of dioxan under stirring and heating. Then 3.09 g of N,N-dicyclohexylcarbodiimide dissolved in 20 ml of dioxan are added dropwise in a nitrogen atmosphere. After cooling the crystals were filtered off and the filtrate was evaporated on a rotary evaporator. The residue was dissolved in 100 ml of ethyl acetate under a nitrogen atmosphere and washed with 100 ml of water. The solution was then evaporated on a rotary evaporator to yield 4.63 g of product (theory 5.58 g). The product was crystallized from 50 ml of ethanol and 60 mg of pure product obtained. M.p.: 51.4° C.

EXAMPLE 13

Preparation of N-(2-Nitratobutyrl)-cysteine ethyl ester 2-nitratobutyric acid (5 g), 8.59 g of cysteine ethyl ester HCl and a catalytic amount of dimethylaminopyridine were dissolved in 100 ml of dioxan under heating and stirring in a nitrogen atmosphere. Then 9.49 g of N,N-dicyclohexylcarbodiimide in 80 ml of dioxan are added dropwise. The reaction mixture is stirred overnight and filtered. The filtrate was evaporated on a rotary evaporator. The residue was dissolved in ethyl acetate and washed with water. The solution was then evaporated on a rotary evaporator to yield 8.03 g of an oily product (9.24 g theory).

EXAMPLE 14

Preparation of N-(3-Nitratobutyryl)-S-acetyl-cysteine ethyl ester

Seven grams of N-(3-nitratobutyryl)-cysteine ethyl ester are dissolved in 150 ml of dichloromethane. Then 27.9 ml of acetic anhydride are slowly added at 5°–10° C. under a nitrogen atmosphere. A solution of 30.4 g of triethylamine in 100 ml of dichloromethane is added dropwise. The mixture is then stirred overnight and then washed with a sodium bicarbonate solution and subsequently with water. The solution is then carefully evaporated on a rotary evaporator. Yield: 9.8 g. The product is crystallized from 50 ml of ethanol. Yield: 3.13 g; 38.84% of theory. M.p.: 81.9° C.

EXAMPLE 15

Preparation of N-(3-Nitratopivaloyl)-S-benzoyl-cysteine ethyl ester 10 g of N-(3-nitratopivaloyl)-cysteine ethyl ester are dissolved in 100 ml of dichloromethane at 5°–10° C. under a nitrogen atmosphere. Subsequently, 4.8 ml of benzoyl chloride are added dropwise. 4.7 ml of triethylamine dissolved in 50 ml of dichloromethane are added dropwise at 5°–10° C. The reaction mixture is stirred for three days. Ice water is added, the organic phase is separated and evaporated. The product is purified by column chromatography using a mixture of 75 parts of methanol and 25 parts of water as the elutant. The eluted fraction is evaporated on a rotary evaporator. Yield: 10.7 g of purified oily product; 79% of theory.

EXAMPLE 16

Preparation of N-(2-Nitratoisobutyryl)-L-cysteine ethyl ester

First Step

Nitration of 2-hydroxyisobutyric acid ethyl ester 16.6 ml concentrated nitric acid at 10°–15° C. are added dropwise to a solution of 26.5 g of 2-hydroxyisobutyric acid ethyl ester in 250 ml of dichloromethane. The solution is cooled to 0°–5° C. and at this temperature 37.5 ml of acetic anhydride were added dropwise. The solution is stirred overnight at room temperature and then 500 ml of ice water are added. The organic phase is separated and successively washed with 100 ml of water, 100 ml of an aqueous concentrated sodium bicarbonate solution and 100 ml of water. The dichloromethane is removed by use of a rotary evaporator. Yield: 34 g of the product as an oil; 96% of theory.

Second Step

Saponification of 2-Nitratoisobutyric acid ethyl ester 30.4 g of 2-nitratoisobutyric acid ethyl ester are dissolved in 120 ml of ethanol. Then a solution of 13.7 g of sodium hydroxide in 100 ml of water is added. The resulting mixture is stirred for 4 hours at room temperature and then neutralized by the addition of 29 ml of 37% hydrochloric acid. After evaporation on a rotary evaporator the residue (21 g) is suspended in 75 ml of boiling n-hexane and filtered. The product is isolated by crystallization at room temperature. Yield: 18.99 g; 66.1% of theory.

Third Step

Preparation of N-(2-Nitratoisobutyryl)-cysteine ethyl ester

A solution of 14.5 g of dicyclohexylcarbodiimide (DCC) in 50 ml of dichloromethane at 5°–10° C. is added dropwise to a solution of 8.7 g of 2-nitratoisobutyric acid and 9.6 g of cysteine ethyl ester in 50 ml of dichloromethane. The mixture is stirred for four days at room temperature, the DCC-urea is filtered off and the filtrate is washed with 100 ml of 1N hydrochloric acid and 100 ml of water. The dichloromethane is removed by use of a rotary evaporator, yielding an oily residue which was purified twice by column chromatography using 765 g of kieselgel Li Chroprep RP18 and 70 methanol/30 water as the eluting solvent. Yield: 1.48 g of oil; 9.1% of theory.

EXAMPLE 17

Preparation of N-(2-Nitratoisobutyryl)-L-methione ethyl ester

N-(2-nitratoisobutyryl)-L-methione ethyl ester was produced using the following materials:

| | |
|---|---|
| 1. L-methione ethyl ester base | 10.6 g |
| 2. 2-nitratoisobutyric acid | 8.9 g |
| 3. Dicyclohexylcarbodiimide (98%) | 13 g |
| 4. Dimethylaminopyridine | 20 mg |
| 5. Dichloromethane | 185 ml |

The process of Example 16, Third Step, was followed using L-methione ethyl ester instead of cysteine ethyl ester. Yield: 20.53 g of a light yellow oil; 111% of theory.

The resulting product contained about 10% of a —O—NO$_2$-containing impurity. A solution was prepared by dissolving 20.5 g of the oil in 51.5 ml of methanol and 20 ml of distilled water for purification by column chromatography. (See Example 16, Third Step). 16.75 g of the product as a colorless oil were obtained. Yield: 90.5% of theory.

EXAMPLE 18

Preparation of N-(3-Nitratopivaloyl)-S-isobutyryl-L-cysteine ethyl ester

N-(3-nitratopivaloyl)-S-isobutyryl-L-cysteine ethyl ester was prepared using the following materials:

| | |
|---|---|
| 1. 3-Nitratopivaloyl-L-cysteine ethyl ester | 10.3 g |
| 2. Isobutyric anhydride | 6.7 g |
| 3. Triethylamine (D = 0.73) | 5 g |
| 4. Dichloromethane | 60 ml |

The process of Example 11 was followed.

3-Nitratopivaloyl-L-cysteine ethyl ester (10.3 mg) and 6.7 g of isobutyric anhydride are combined in 60 ml of dichloromethane at room temperature in a nitrogen atmosphere with stirring. Then 5 g of triethylamine in dichloromethane is added dropwise under stirring. After the end of the reaction, the solution is washed with 1N HCl, 10% aqueous sodium bicarbonate solution and water. The dichloromethane extract is evaporated to dryness on a rotavapor. 10.4 grams (81.6% of theory) of an oily product is obtained. The identity of the product is verified by mass spectroscopy.

PHARMACOLOGICAL ACTIVITY TESTING

The pharmacological action of the compounds provided by the invention is illustrated further by the following experiments.

Pharmacological Experiment Method 1

Administration of new organic nitrates to detect the nitrate action on the circulatory parameters of a dog that is awake.

The purpose of the test is to determine how the new organic nitrates act on various circulatory parameters of a dog that is awake after intravenous or oral administration. All experiments were carried out on trained beagle dogs; the circulatory parameters were measured with an arterial catheter tip manometer and a balloon catheter introduced into the V. jugularis. In order to describe the action on the arterial system, the systolic, mean and diastolic blood pressure (BP) and heart rate (HR) were measured. From these, the peripheral resistance (TPR) and the extensibility of the arterial air chamber (COMPL) were calculated. The low pressure system was measured through the central venous pressure (CVP) and the pulmonary arterial pressure (PAP). The control or reference product used was isosorbid-5-mononitrate (ISM-5).

DESCRIPTION OF THE DRAWINGS

The drawing figures illustrate graphically the activity spectrum of specific organic nitrates.

The abbreviations used in the drawings have the following meanings:
CO means cardiac output
SV means stroke volume
BP means diastolic blood pressure
HR means heart rate
CVP means central venous pressure
PAP means pulmonary arterial pressure
COMPL means extensibility of the arterial air chamber
TPR means peripheral resistance
In "Mean±sem.N=5" for example, mean is mean value, sem. is standard error of the mean, and N is the number of errors of the mean value.

FIGS. 1 to 8 show the action of orally and intravenously administered ISM-5. After administration by each route, the ISM-5 caused a slight decrease in systolic blood pressure, the mean pressure was hardly effected, the extensibility of the air chamber increased significantly and the low pressure system pressure decreased.

Figure 1:
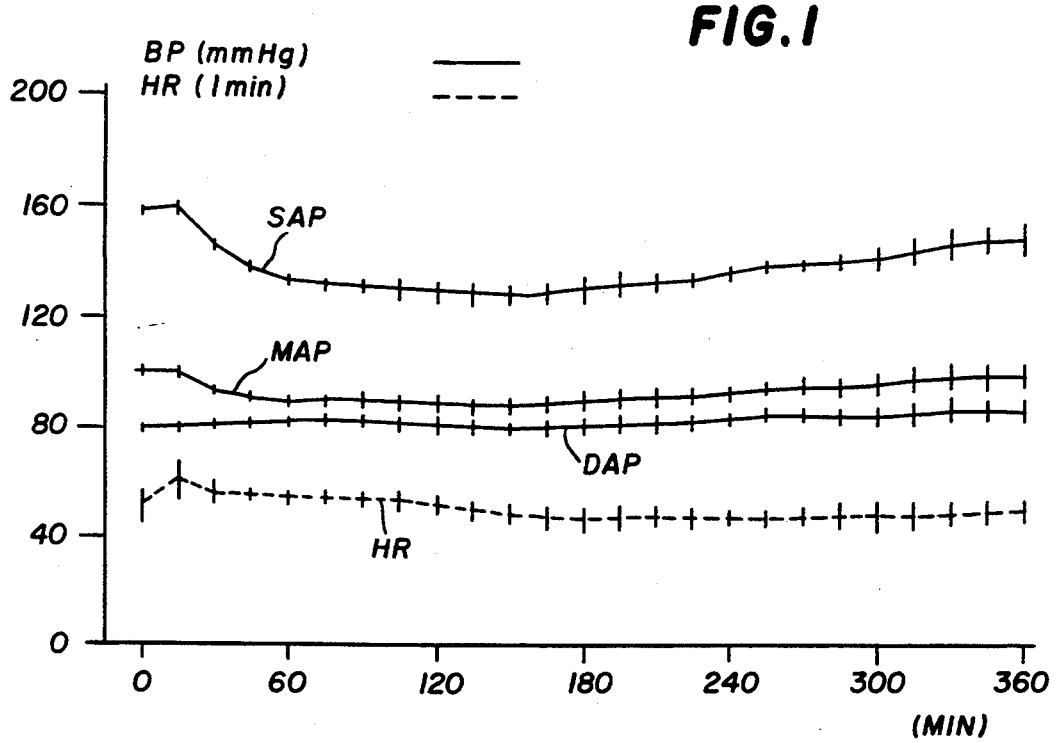
Figure 2:
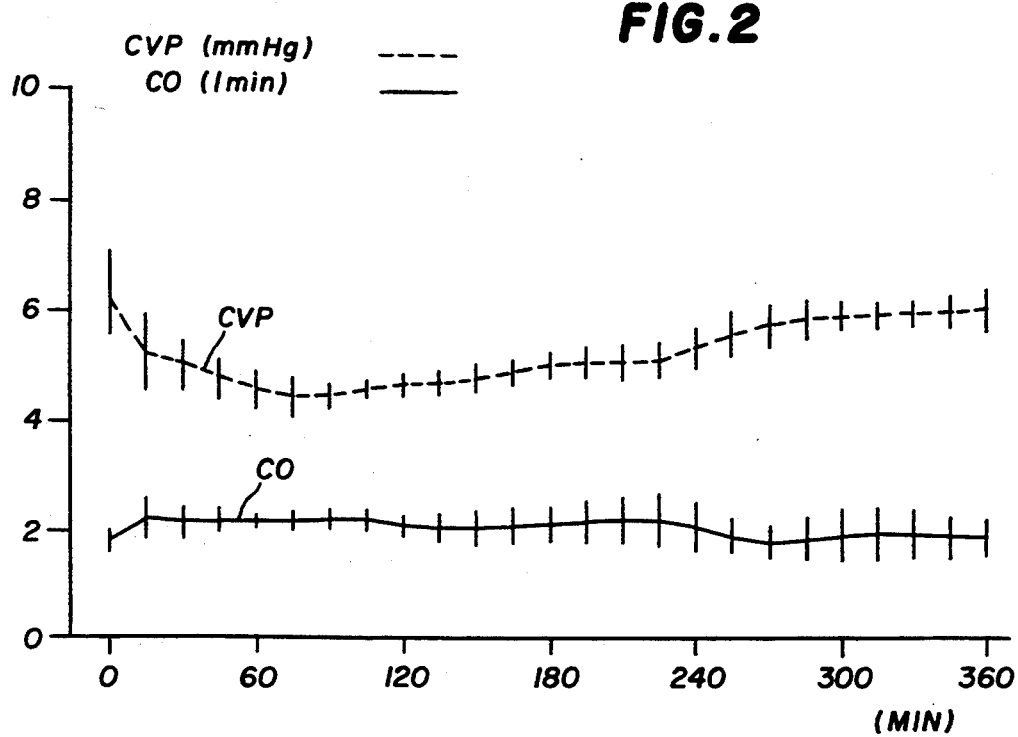
Figure 3:
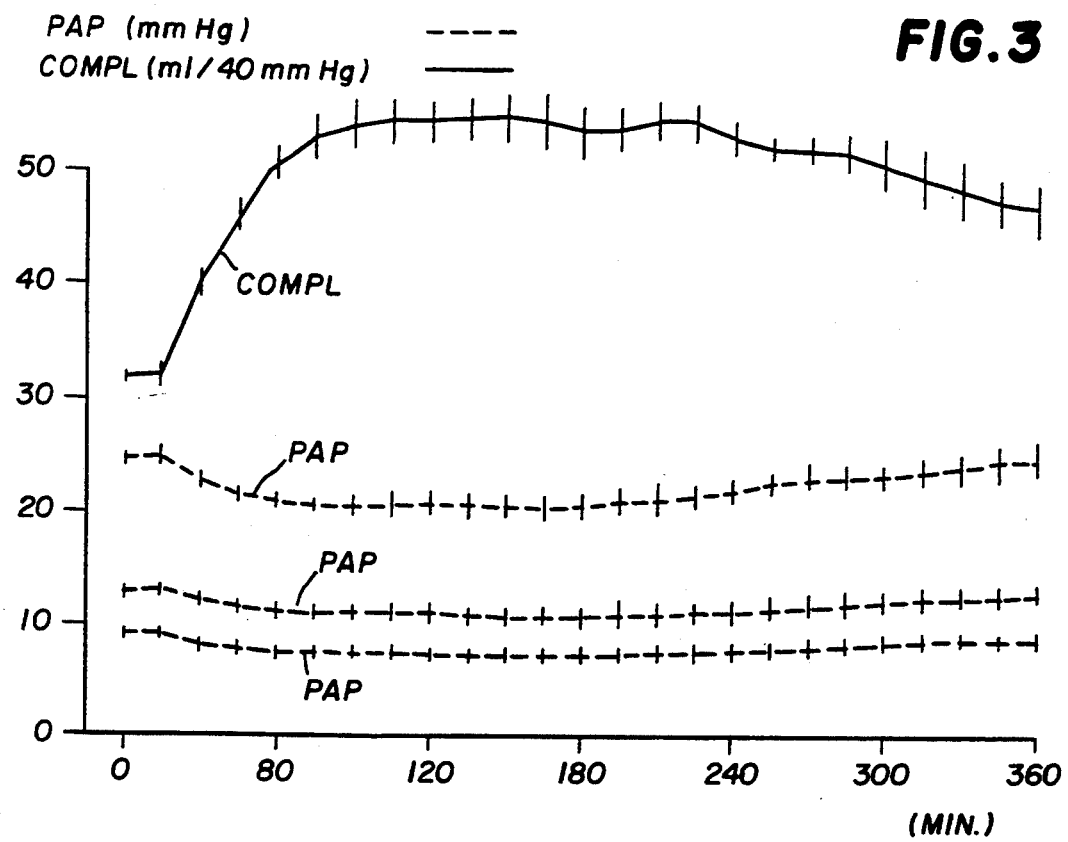
Figure 4:
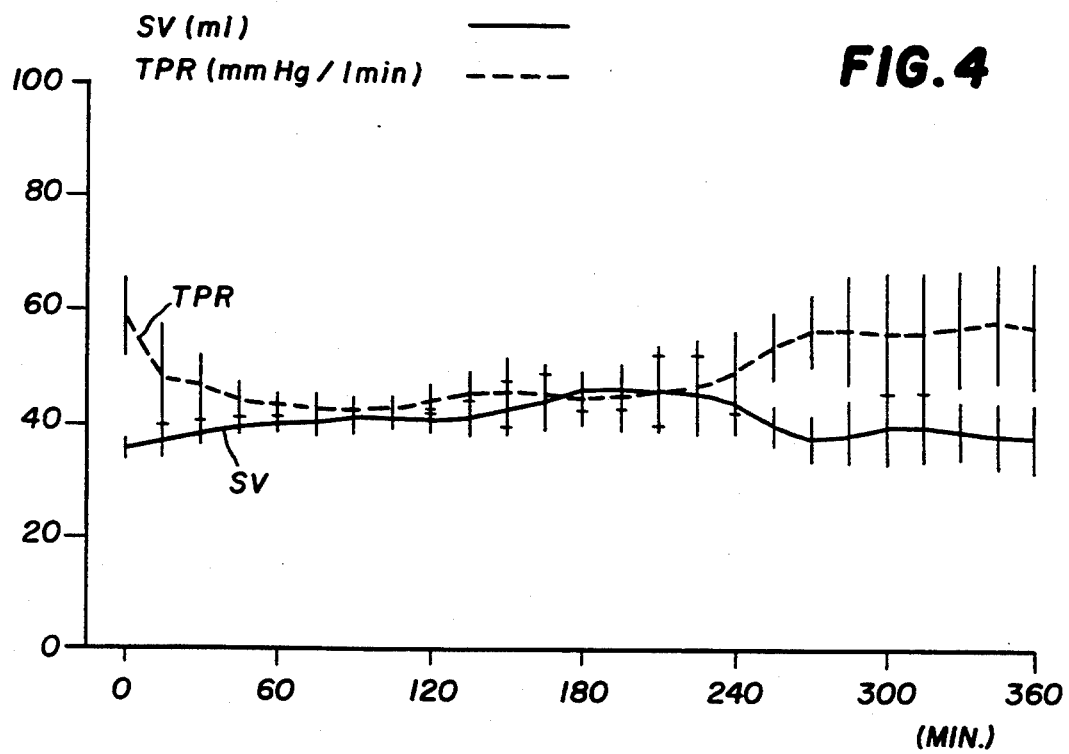
Figure 9:
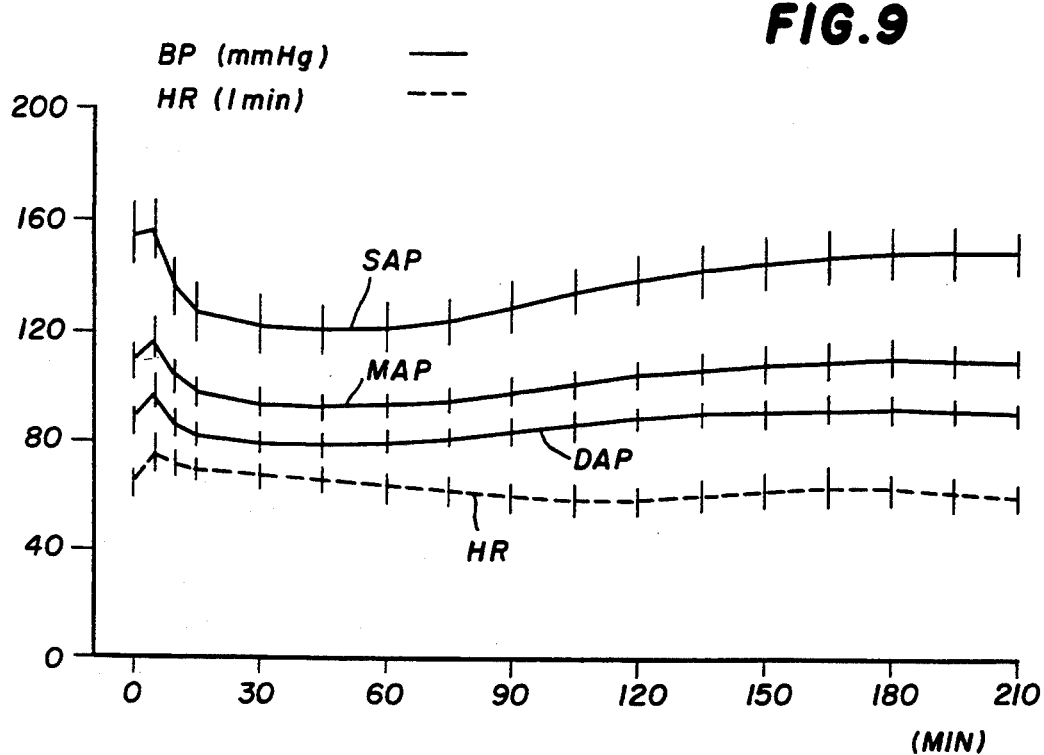
FIGS. 9 to 16 show the corresponding effects of N-(3-nitratopivaloyl)-methionine ethyl ester (Nitrato-Piv-Meth-Et) for the corresponding circulatory areas. Here, again, the comparison between intravenous and oral administration indicates good bioavailability.
Figure 10:
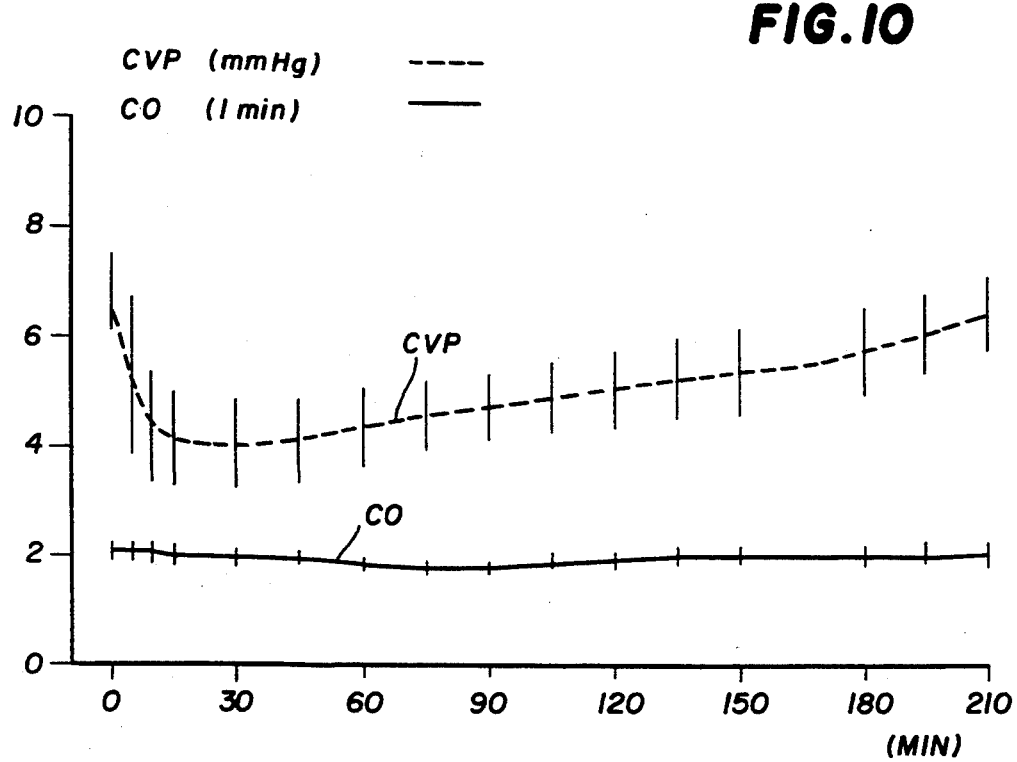
Figure 11:
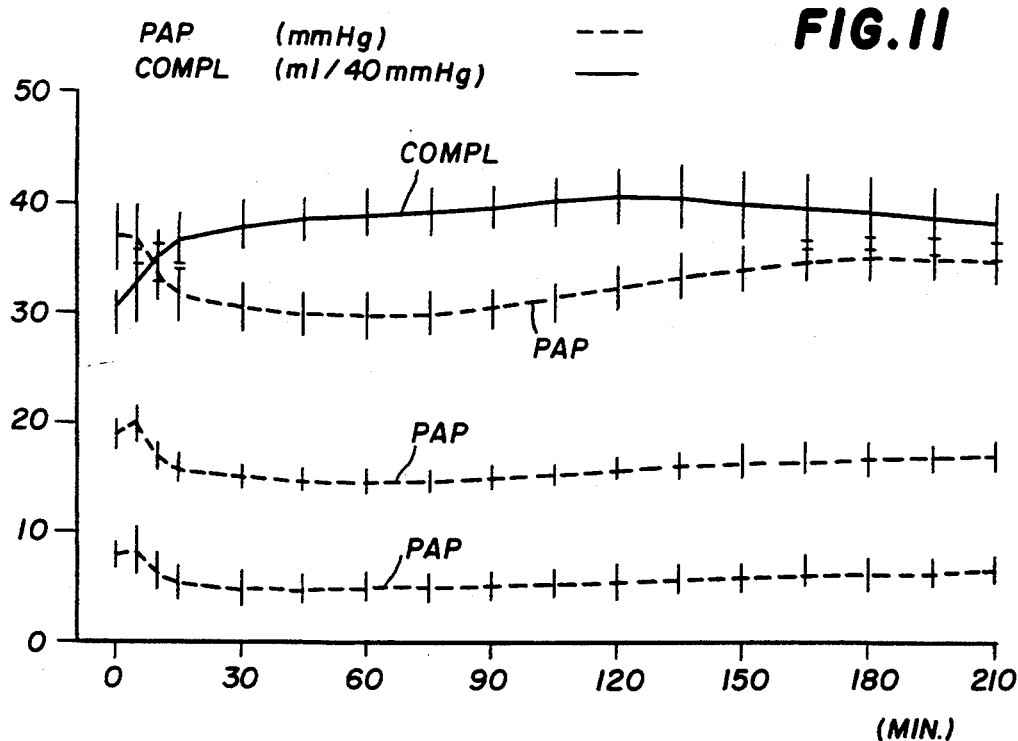
Figure 12:
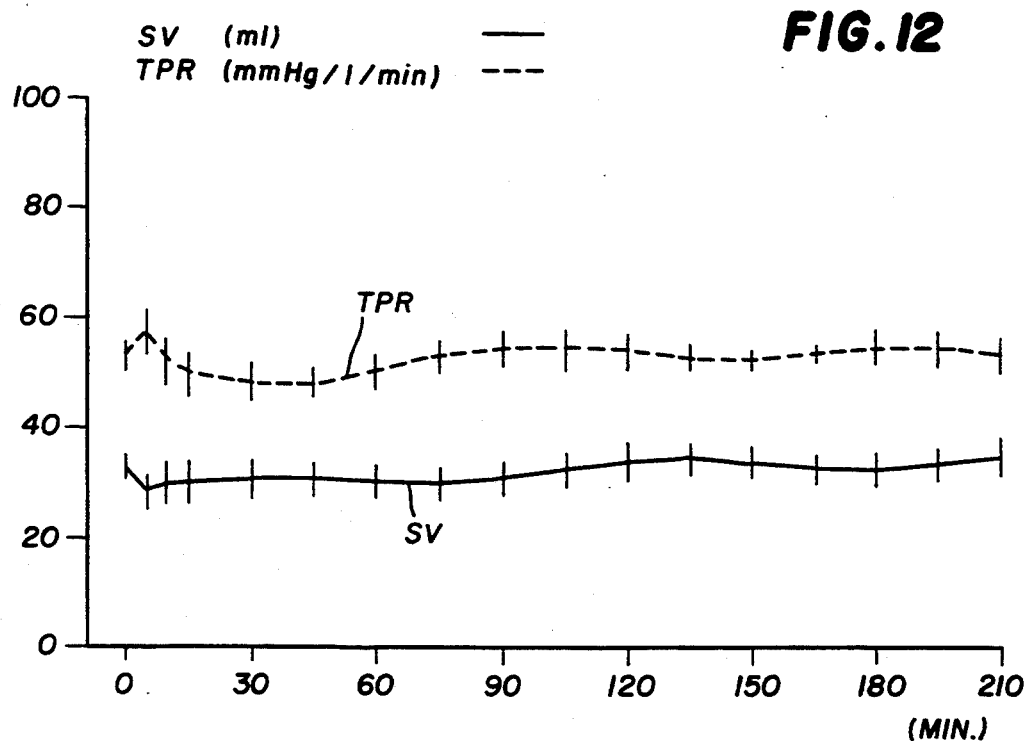
Figure 13:
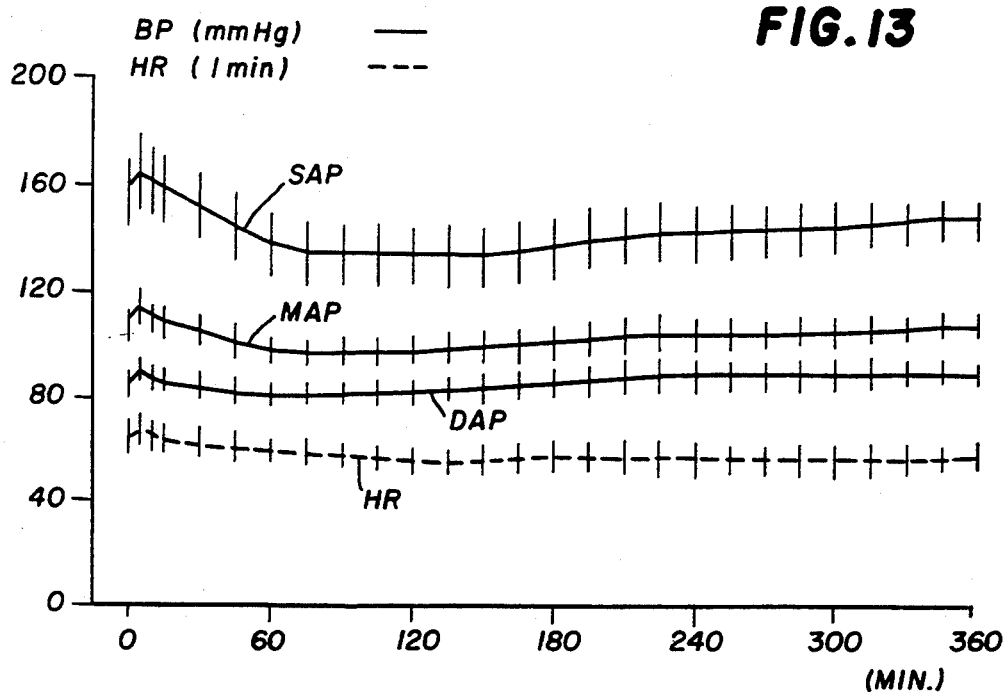
Figure 14:
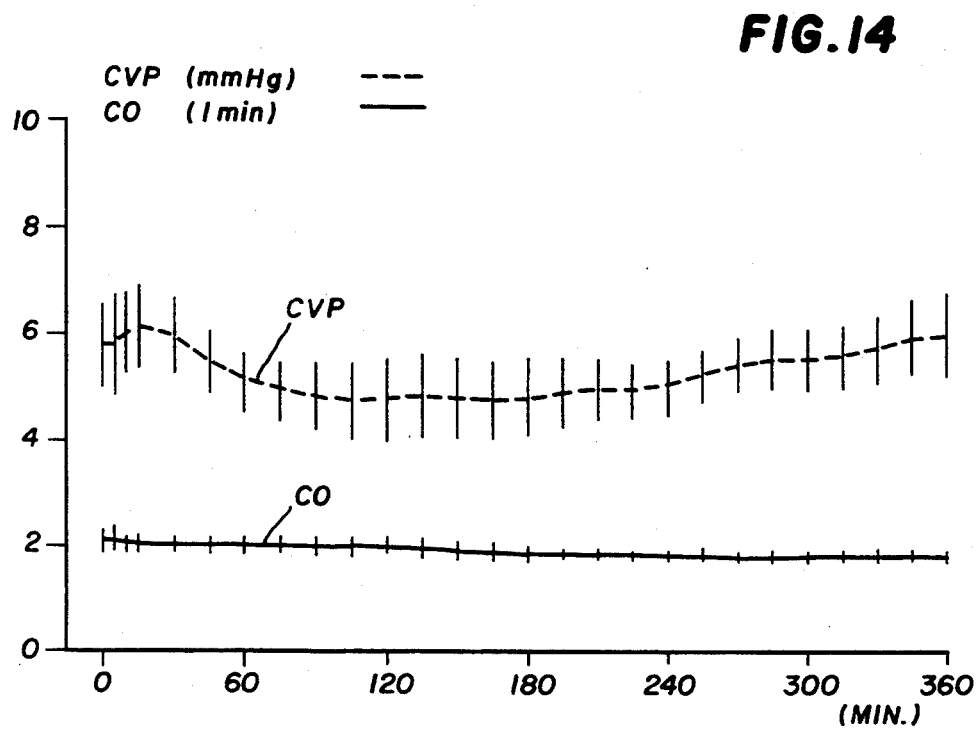
Figure 15:
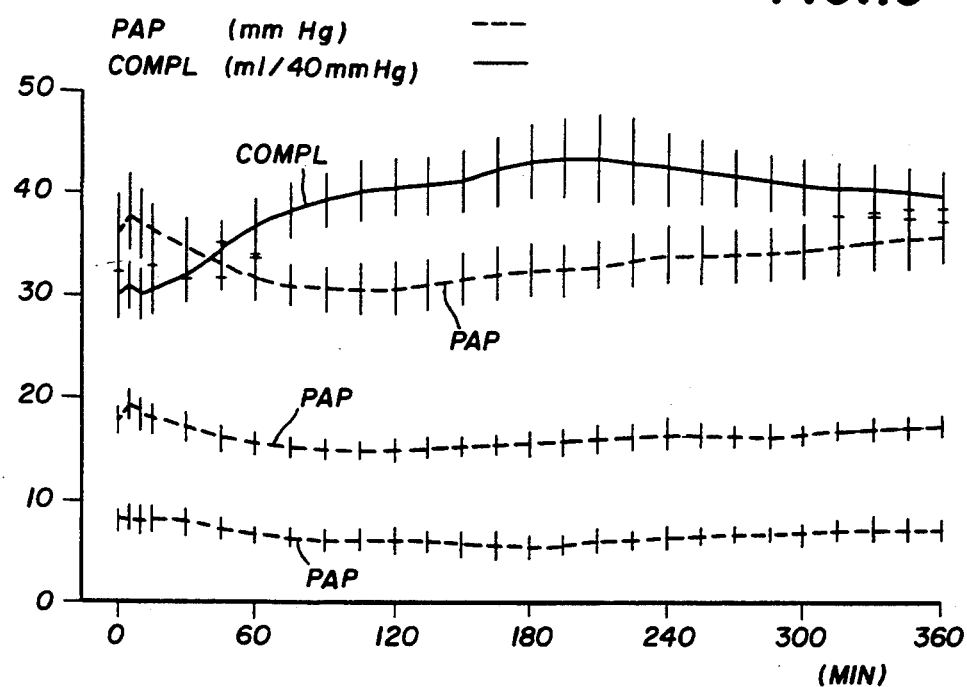
Figure 16:
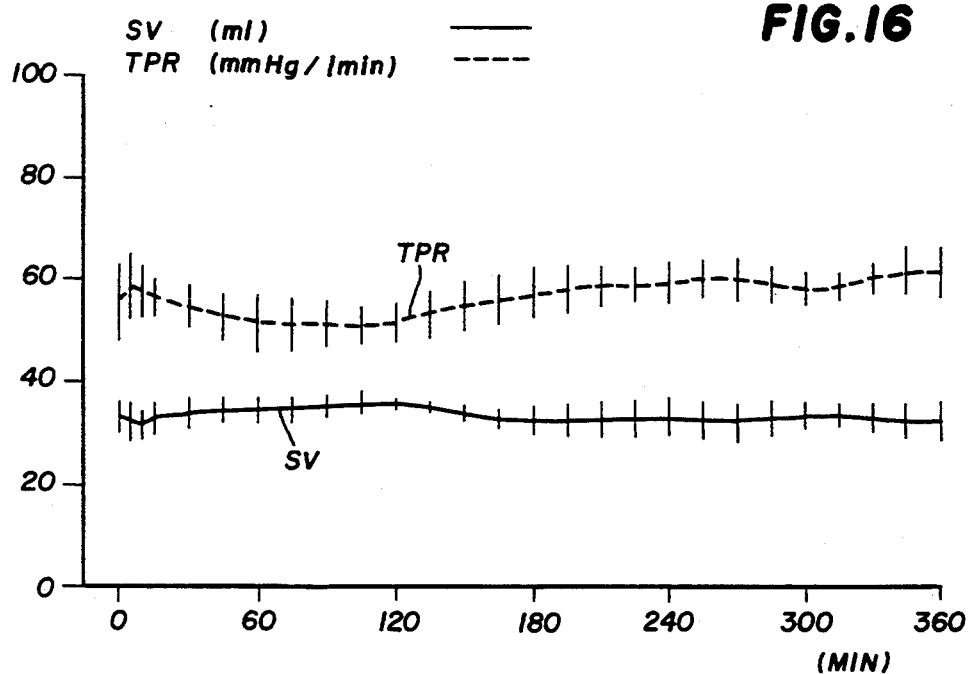

The novel substance N-(3-nitratopivaloyl)-cysteine ethyl ester was also tested and it shows good bioavailability and a course of action typical of a nitrate.

The results for both of the tested novel compounds show they have an action which is comparable to that of ISM-5 and have good bioavailability.

Pharmacological Experiment Method 2

Determining the lack of tolerance to the action of new organic nitrates on increasing coronary flow in isolated perfused heart.

The purpose of the present investigation was to study the action and the development of tolerance to new organic nitrate compounds on isolated perfused rat heart. For this purpose, a rat heart was isolated and prepared as a "working heart".

In this experimental arrangement, the heart performs defined circulatory work from which a defined oxygen consumption and coronary flow result. The action of nitrate-like compounds can be measured in this model by the drug-induced coronary flow increase.

The resistance of the coronary vessels on an isolated working rat heart was chosen as the parameter for the detection of the action of the nitrate. A rat heart with a weight of about one gram is perfused through the left auricle with a plasma-like solution which contains nutrients and is saturated with oxygen. The left ventricle pumps the solution into the aorta against a defined pressure. Corresponding to the physiological conditions, a part of this solution flows through the coronary vessels for supplying the heart itself. At a defined work of the heart, this fraction, from which the coronary resistance can be calculated, is constant. The addition of a nitrate or other coronary dilating drug causes a drop in this coronary resistance. Therefore, if a constant concentration of an organic nitrate is introduced to the heart, then, after an initial decrease of the resistance, a partial loss of activity occurs within 20 minutes. On this model, the substances also show a coronary dilating effect, but this is not followed by a loss in activity. The maximum drop of the coronary resistance is still completely present after 60 minutes. The tested compounds were compared in an equimolar dosage with $10^{-4}$M nitroglycerin trinitrate. Continuous infusion of nitroglycerin causes a rapid coronary flow increase by 7.6±1.88 ml/min $g_{ww}$ ($\bar{x}$±SD). Within 20 minutes, the flow decreases by 55.9%. Upon further perfusion, the action of nitroglycerin is unchanged. In this experimental model, the new nitrates also show a coronary flow increase, but this is followed by only a very slight drop in the activity. This result indicates that the described new compounds do not show the tolerance behavior as do conventional nitrates.

TABLE 1

Action of new organic nitrates in comparison to nitroglycerin on the coronary flow in isolated perfused rat hearts. x ± SEM, n = 7

|  | Maximum Coronary Activity Increase (ml/min $g_{ww}$) | Drop in flow (%) |
|---|---|---|
| 100 μM nitroglycerine | 7.6 ± 0.71 | 56.0 |
| 100 μM N-(3-nitratopivaloyl)-cysteine ethyl ester | 6.6 ± 0.88 | 5.2 |
| 100 μM N-(3-nitratopivaloyl)-methionine ethyl ester | 8.3 ± 0.92 | 7.0 |

Finally, the action of N-(3-nitratopivaloyl)-cysteine ethyl ester (Nitrato-Piv-Cy-Et) was characterized on guinea pig heart. Nitrato-Piv-Cy-Et leads to a concentration-dependent increase of the coronary flow in a working heart model (guinea pig heart) even in a very low dose range. A flow increase of 25% is achieved even with 380 µg of nitrato-Piv-Cy-Et per liter of perfusion medium, corresponding to 1.3 µmole per liter. The corresponding concentration for glycerol trinitrate (GTN) with 5 mg/liter is at least a factor of 12 times higher. Thus, in the case of Nitrato-Piv-Cy-Et we are dealing with an especially active compound with regard to the vessels. No weakening of the coronary dilating effect as a manifestation of tolerance development could be observed at any dose during a one hour drenching perfusion. It can be concluded from this that Nitrato-Piv-Cy-ET does not produce any vessel tolerance, in contrast to GTN.

On isolated guanyl cyclase, Nitrato-Piv-Cy-Et leads to a concentration-dependent activation of the enzyme, corresponding to enhanced formation of cGMP per unit time. The special characteristic of this compound in comparison to the classical organic nitro compounds is that the activation occurs in vitro even in the absence of cysteine. This explains at the same time the observation that Nitrato-Piv-Cy-ET and the other chemical compounds, for example, those in the "Working Heart Model", do not cause any tolerance, a finding which is of especially great practical importance for clinical long-term administration. The concentration necessary for one-half of the maximum activity ($ED_{50}$) of guanyl cyclase is around 200 µmole/liter. The corresponding value for GTN (in the presence of 5 mmoles/liter of cysteine) is approximately 80 µmoles/liter.

What is claimed is:

1. Compounds of the formula

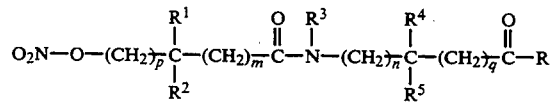

wherein:
R represents hydroxy, lower alkoxy, lower alkenoxy, di-lower alkylamino-lower alkoxy, acylamino-lower alkoxy, acyloxy-lower alkoxy, aryloxy, aryl-lower alkyloxy, substituted aryloxy or substituted aryl-lower alkoxy groups, where the substituent is a member of the group consisting of methyl, methoxy and halogen; amino, lower alkylamino, di-lower alkylamino, aryl-lower alkylamino, hydroxy-lower alkylamino or amino acid groups through peptide bonds, $R^1$ represents hydrogen, alkyl with 1 to 6 carbon atoms, substituted lower alkyl, where the substituent is a member of the group consisting of halogen, groups defined by R containing hydroxy, lower alkoxy, aryloxy, amino, lower alkylamino, acylamino, acyloxy, arylamino, mercapto, lower alkylthio and arylthio, $R^2$ represents hydrogen, lower alkyl and the groups represented by $R^1$, $R^3$ represents hydrogen and lower alkyl, $R^4$ represents hydrogen, lower alkyl, phenyl, methoxyphenyl, phenyl-lower alkyl, methoxyphenyl-lower alkyl, hydroxyphenyl-lower alkyl, hydroxy lower alkyl, alkoxy lower alkyl, amino-lower alkyl, acylamino lower alkyl, mercapto-lower alkyl and lower alkylthio-lower alkyl, $R^5$ represents lower alkylthiol, —SH and S-acyls of alkylthiol and —SH and particularly —S-acetyl, —S-propionyl, —S-butyryl, —S-isobutyryl, —S-caproyl, —S-capryl, —S-pivaloyl and —S-benzoyl, lower alkyl —S—C—O—$R^6$, lower alkyl —S—C—N—$R^6$, lower alkylthio-lower alkanoic acid and esters and amides thereof, and lower alkylthio-lower alkyl, wherein $R^6$ represents hydrogen and lower alkyl, groups in which R and $R^5$ are bonded together and form part of a thiolactone group, m, n and q are whole numbers from 0 to 10, p is 0 or 1, and pharmaceutically acceptable salts thereof.

2. Compounds according to claim 1 in which the nitrato alkanoic acid components have a chain length of $C_2$-$C_6$, and are selected from the group consisting of straight-chain, branched chain, racemic and optical isomers.

3. A compound according to claim 1 or 2 in which the amino acid is a member of the group consisting of cysteine, methionine and homocysteine.

4. A compound according to claim 1 or 2 in which the amino acid is in the stereochemical L-form.

5. A compound according to claim 1 or 2 in which an amino acid selected from the group consisting of cysteine and methionine is present as an ester selected from the group consisting of methyl, ethyl and propyl esters.

6. A compound according to claim 3 in which cysteine is esterified on the SH group with an alkanoic acid having a chain length of $C_2$-$C_8$.

7. A compound according to claim 1 or 2 selected from the group consisting of:
N-(2-nitratoacetyl)-cysteine ethyl ester
N-(2-nitratoacetyl)-S-acetyl-cysteine ethyl ester
N-(2-nitratoacetyl)-S-propionyl-cysteine ethyl ester
N-(2-nitratoacetyl)-S-pivaloyl-cysteine ethyl ester
N-(2-nitratoacetyl)-methionine methyl ester
N-(2-nitratopropionyl)-cysteine
N-(2-nitratopropionyl)-cysteine ethyl ester
N-(2-nitratopropionyl)-methionine ethyl ester
N-(2-nitratobutyryl)-cysteine
N-(2-nitratobutyryl)-cysteine ethyl ester
N-(2-nitratobutyryl)-S-acetyl-cysteine ethyl ester
N-(2-nitratobutyryl)-S-butyryl-cysteine ethyl ester
N-(2-nitratobutyryl)-methionine ethyl ester
N-(2-nitratoisobutyryl)-cysteine
N-(2-nitratoisobutyryl)-cysteine ethyl ester
N-(2-nitratoisobutyryl)-S-benzoyl-cysteine ethyl ester
N-(2-nitratoisobutyryl)-S-acetyl-cysteine ethyl ester
N-(2-nitratoisobutyryl)-S-pivaloyl-cysteine ethyl ester
N-(2-nitratoisobutyryl)-methionine ethyl ester
N-(3-nitratobutyryl)-cysteine
N-(3-nitratobutyryl)-cysteine ethyl ester
N-(3-nitratobutyryl)-cysteine ethyl ester-S-carbonate
N-(3-nitratobutyryl)-S-acetyl-cysteine ethyl ester
N-(3-nitratobutyryl)-S-propionyl-cysteine ethyl ester
N-(3-nitratobutyryl)-methionine ethyl ester
N-(3-nitratobutyryl)-homocysteine thiolactone
N-(3-nitratopivaloyl)-cysteine
N-(3-nitratopivaloyl)-cysteine ethyl ester
N-(3-nitratopivaloyl)-cysteine ethyl ester-S-carbonate
N-(3-nitratopivaloyl)-S-acetyl-cysteine ethyl ester
N-(3-nitratopivaloyl)-S-propionyl-cysteine ethyl ester
N-(3-nitratopivaloyl)-S-butyryl-cysteine ethyl ester
N-(3-nitratopivaloyl)-S-isobutyryl-cysteine ethyl ester
N-(3-nitratopivaloyl)-S-pivaloyl-cysteine ethyl ester
N-(3-nitratopivaloyl)-S-benzoyl-cysteine ethyl ester
N-(3-nitratopivaloyl)-methionine ethyl ester
N-(3-nitratopivaloyl)-methionine N-(3-nitratopivaloyl)-homocysteine thiolactone
N-(2-nitratohexanoyl)-cysteine ethyl ester
N-(2-nitratohexanoyl)-S-propionyl-cysteine ethyl ester
N-(3-nitratohexanoyl)-cysteine ethyl ester
N-(3-nitratohexanoyl)-methionine methyl ester
N-(12-nitratolauroyl)-cysteine
N-(12-nitratolauroyl)-cysteine ethyl ester
N-(12-nitratolauroyl)-S-acetyl-cysteine and N-(12-nitratolauroyl)-S-pivaloyl-cysteine.

8. A pharmaceutical composition comprising as an active ingredient a compound as defined in claim 1 and a nontoxic liquid pharmaceutical carrier and the pharmaceutical composition contains about 1 to 40 mg of active compound per liter.

9. A pharmaceutical composition comprising as an active ingredient a compound as defined in claim 1 and a nontoxic pharmaceutical carrier in unit dosage form in which the pharmaceutical carrier is a solid and the pharmaceutical composition contains about 1 to 500 mg per unit dosage form.

10. A pharmaceutical composition according to claim 8 or 9 in which the compound is selected from the group consisting of:
N-(2-nitratoacetyl)-cysteine
N-(2-nitratoacetyl)-S-acetyl-cysteine
N-(2-nitratoacetyl)-S-propionyl-cysteine
N-(2-nitratoacetyl)-S-pivaloyl-cysteine
N-(2-nitratoacetyl)-methionine
N-(2-nitratopropionyl)-cysteine
N-(2-nitratopropionyl)-methionine
N-(2-nitratobutyryl)-cysteine
N-(2-nitratobutyryl)-S-acetyl-cysteine
N-(2-nitratobutyryl)-S-butyryl-cysteine
N-(2-nitratobutyryl)-methionine
N-(2-nitratoisobutyryl)-cysteine
N-(2-nitratoisobutyryl)-S-benzoyl-cysteine
N-(2-nitratoisobutyryl)-S-acetyl-cysteine
N-(2-nitratoisobutyryl)-S-pivaloyl-cysteine
N-(2-nitratoisobutyryl)-methionine
N-(3-nitratobutyryl)-cysteine
N-(3-nitratobutyryl)-S-acetyl-cysteine
N-(3-nitratobutyryl)-S-propionyl-cysteine
N-(3-nitratobutyryl)-methionine
N-(3-nitratobutyryl)-homocysteine thiolactone
N-(3-nitratopivaloyl)-cysteine
N-(3-nitratopivaloyl)-cysteine-S-carbonate
N-(3-nitratopivaloyl)-S-acetyl-cysteine
N-(3-nitratopivaloyl)-S-propionyl-cysteine
N-(3-nitratopivaloyl)-S-butyryl-cysteine
N-(3-nitratopivaloyl)-S-isobutyryl-cysteine
N-(3-nitratopivaloyl)-S-pivaloyl-cysteine
N-(3-nitratopivaloyl)-S-benzoyl-cysteine
N-(3-nitratopivaloyl)-methionine
N-(3-nitratopivaloyl)-homocysteine thiolactone
N-(2-nitratohexanoyl)-cysteine
N-(2-nitratohexanoyl)-S-propionyl-cysteine
N-(3-nitratohexanoyl)-cysteine
N-(3-nitratohexanoyl)-methionine
N-(12-nitratolauroyl)-cysteine
N-(12-nitratolauroyl)-S-acetyl-cysteine
N-(12-nitratolauroyl)-S-pivaloyl-cysteine,
esters thereof, and nontoxic acid addition salts thereof.

11. A method of treating a patient to treat angina pectoris, effect coronary dilation, reduce blood pressure, treat heart insufficiency, dilate peripheral vessels, enhance arterial compliance, and reduce total peripheral resistance comprising administering to the patient a pharmaceutical composition containing as an active ingredient a compound as defined in claim 1 and a nontoxic pharmaceutical carrier with said compound being present in the said composition in an amount effective for treating said patient.

12. A method according to claim 11 in which the pharmaceutical carrier is a liquid and the pharmaceutical composition contains about 1 to 40 mg of active compound per liter.

13. A method according to claim 11 in which the pharmaceutical composition is in unit dosage form, the pharmaceutical carrier is a solid and the pharmaceutical composition contains about 1 to 500 mg per unit dosage form.

14. A method according to claim 11 in which the active compound is selected from the group consisting of:
N-(2-nitratoacetyl)-cysteine
N-(2-nitratoacetyl)-S-acetyl-cysteine
N-(2-nitratoacetyl)-S-propionyl-cysteine
N-(2-nitratoacetyl)-S-pivaloyl-cysteine
N-(2-nitratoacetyl)-methionine
N-(2-nitratopropionyl)-cysteine
N-(2-nitratopropionyl)-methionine
N-(2-nitratobutyryl)-cysteine
N-(2-nitratobutyryl)-S-acetyl-cysteine
N-(2-nitratobutyryl)-S-butyryl-cysteine
N-(2-nitratobutyryl)-methionine
N-(2-nitratoisobutyryl)-cysteine
N-(2-nitratoisobutyryl)-S-benzoyl-cysteine
N-(2-nitratoisobutyryl)-S-acetyl-cysteine
N-(2-nitratoisobutyryl)-S-pivaloyl-cysteine
N-(2-nitratoisobutyryl)-methionine
N-(3-nitratobutyryl)-cysteine
N-(3-nitratobutyryl)-S-acetyl-cysteine
N-(3-nitratobutyryl)-S-propionyl-cysteine
N-(3-nitratobutyryl)-methionine
N-(3-nitratobutyryl)-homocysteine thiolactone
N-(3-nitratopivaloyl)-cysteine
N-(3-nitratopivaloyl)-cysteine-S-carbonate
N-(3-nitratopivaloyl)-S-acetyl-cysteine
N-(3-nitratopivaloyl)-S-propionyl-cysteine
N-(3-nitratopivaloyl)-S-butyryl-cysteine
N-(3-nitratopivaloyl)-S-isobutyryl-cysteine
N-(3-nitratopivaloyl)-S-pivaloyl-cysteine
N-(3-nitratopivaloyl)-S-benzoyl-cysteine
N-(3-nitratopivaloyl)-methionine
N-(3-nitratopivaloyl)-homocysteine thiolactone
N-(2-nitratohexanoyl)-cysteine
N-(2-nitratohexanoyl)-S-propionyl-cysteine
N-(3-nitratohexanoyl)-cysteine
N-(3-nitratohexanoyl)-methionine
N-(12-nitratolauroyl)-cysteine
N-(12-nitratolauroyl)-S-acetyl-cysteine
N-(12-nitratolauroyl)-S-pivaloyl-cysteine,
esters thereof, and nontoxic acid addition salts thereof.

15. Compounds according to claim 1 in which:
R represents hydroxy and lower alkoxy;
$R^1$ represents hydrogen and alkyl with 1 to 6 carbon atoms;
$R^2$ represents hydrogen and lower alkyl;
$R^3$ represents hydrogen and lower alkyl;
$R^4$ represents hydrogen and lower alkyl;
$R^5$ represents —SH and alkylthiol and S-acyls thereof of the group consisting of —S-acetyl, —S-propionyl, —S-butyryl, —S-isobutyryl, —S-caproyl, —S-capryl, —S-pivaloyl and —S-benzoyl, groups in which R and R⁵ are bonded together and form part of a thiolactone group, m, n and q are the same or different whole numbers from 0 to 3, and p is 0 or 1.

16. Compounds according to claim 15 in which p is 0.

17. Compounds according to claim 15 in which p is 1.

18. A pharmaceutical composition in unit dosage form comprising as an active ingredient about 1 to 500 mg per unit dosage form of a compound of the group consisting of N-(3-nitratobutyryl)-cysteine; N-(3-nitratobutyryl)methionine; N-(3-nitratopivaloyl)-cysteine; N-(3-nitratopivaloyl)-methionine and lower alkyl esters thereof, and a nontoxic solid pharmaceutical carrier.

* * * * *

UNITED STATES PATENT AND TRADEMARK OFFICE
CERTIFICATE OF CORRECTION

PATENT NO. : 5,428,061
DATED : June 27, 1995
INVENTOR(S) : KLAUS SANDROCK ET AL.

It is certified that error appears in the above-identified patent and that said Letters Patent is hereby corrected as shown below:

Column 2, line 43, after "-S-isobutyryl," insert -- -S-carproyl --.

Column 9, line 47, "CHI$_3$" should be --CHCl$_3$--.

Column 9, line 57, "Na2SO$_4$" should be --Na$_2$SO$_4$--.

Column 10, line 14, "N-(12-nitratolaurol)-cysteine" should be -- N-(12-nitratolauroyl)-cysteine --.

Signed and Sealed this

Sixteenth Day of January, 1996

Attest:

BRUCE LEHMAN

Attesting Officer

Commissioner of Patents and Trademarks